(12) United States Patent
Abou Fayad et al.

(10) Patent No.: US 11,365,201 B2
(45) Date of Patent: Jun. 21, 2022

(54) CHLOROTONIL DERIVATIVES

(71) Applicant: HELMHOLTZ-ZENTRUM FÜR INFEKTIONSFORSCHUNG GMBH, Braunschweig (DE)

(72) Inventors: Antione Abou Fayad, Braunschweig (DE); Jennifer Herrmann, Braunschweig (DE); Katrin Jungmann-Sahner, Braunschweig (DE); Rolf Müller, Braunschweig (DE); Kathrin Mohr, Braunschweig (DE); Steffen Bernecker, Braunschweig (DE); Stephan Hüttel, Braunschweig (DE); Rolf Jansen, Braunschweig (DE); Emilia Oueis, Braunschweig (DE); Anastasia Andreas, Braunschweig (DE)

(73) Assignee: Helmholtz-Zentrum Für Infektionsforschung GmbH, Braunschweig (DE)

( * ) Notice: Subject to any disclaimer, the term of this patent is extended or adjusted under 35 U.S.C. 154(b) by 127 days.

(21) Appl. No.: 16/762,458

(22) PCT Filed: Nov. 7, 2018

(86) PCT No.: PCT/EP2018/080489
§ 371 (c)(1),
(2) Date: May 7, 2020

(87) PCT Pub. No.: WO2019/092030
PCT Pub. Date: May 16, 2019

(65) Prior Publication Data
US 2021/0371426 A1    Dec. 2, 2021

(30) Foreign Application Priority Data
Nov. 7, 2017   (EP) ..................................... 17200445

(51) Int. Cl.
C07D 493/04     (2006.01)
C07D 313/00     (2006.01)
A61P 31/04      (2006.01)

(52) U.S. Cl.
CPC ............ C07D 493/04 (2013.01); A61P 31/04 (2018.01); C07D 313/00 (2013.01)

(58) Field of Classification Search
CPC ........................... C07D 493/04; C07D 313/00
See application file for complete search history.

(56) References Cited

FOREIGN PATENT DOCUMENTS

JP       2011010586 A       1/2011

OTHER PUBLICATIONS

Jungmann et al. ACS Chem. Biol. 2015, 10, 2480-2490 (Year: 2015).*
Jungmann, Katrin, et al. "Two of a Kindî-, The Biosynthetic Pathways of Chlorotonil and Anthracimycin." ACS chemical biology 10.11 (2015): 2480-2490 (11 pages).
Gerth, Klaus, et al. "Chlorotonil A, a Macrolide with a Unique gemâ€?Dichloroâ€?1, 3â€?dione Functionality from Sorangium cellulosum, So ce1525." Angewandte Chemie International Edition 47.3 (2008): 600-602 (3 pages).
Held, Jana, et al. "Antimalarial activity of the myxobacterial macrolide chlorotonil A." Antimicrobial agents and chemotherapy 58.11 (2014): 6378-6384 )7 pages).
Rahn, Nicola, and Markus Kalesse. "The total synthesis of chlorotonil A." Angewandte Chemie International Edition 47.3 (2008): 597-599 (3 pages).
Lambros, Chris, and Jerome P. Vanderberg. "Synchronization of Plasmodium falciparum erythrocytic stages in culture." The Journal of parasitology (1979): 418-420 (3 pages).
Trager, William, and James B. Jensen. "Human malaria parasites in continuous culture." Science 193.4254 (1976) 373-675 (3 pages).
Noedl, Harald, et al. "Simple histidine-rich protein 2 double-site sandwich enzyme-linked immunosorbent assay for use in malaria drug sensitivity testing." Antimicrobial agents and chemotherapy 49.8 (2005): 3575-3577 (3 pages).
Team, R. Core. "R: A Language and Environment for Statistical Computing http://www." R-project.org (2014).
International Search Report of PCT/EP2018/080489. 2018.

* cited by examiner

*Primary Examiner* — Matthew P Coughlin
(74) *Attorney, Agent, or Firm* — Fox Rothschild LLP

(57) ABSTRACT

The present invention relates to novel chlorotonil derivatives of formula (I) and the use thereof for the treatment or prophylaxis of bacterial infections and malaria.

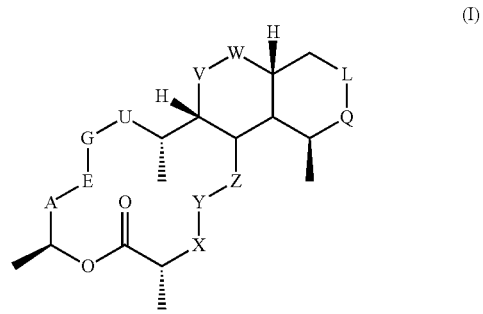

(I)

17 Claims, No Drawings

CHLOROTONIL DERIVATIVES

CROSS-REFERENCES TO RELATED APPLICATIONS

This application is a 35 U.S.C. § 371 U.S. national entry of International Application No. PCT/EP2018/080489, having an International filing date of Nov. 17, 2018 which claims under 35 U.S.C. § 119 the benefit of European Patent Application 17200445.9 filed on Nov. 7, 2017.

The present invention provides novel chlorotonil derivatives and the use thereof for the treatment or prophylaxis of bacterial infections and malaria.

The present invention relates to the field of infectious diseases caused by bacterial pathogens and plasmodia parasites and the need of novel antibiotics for therapeutic applications. It precisely tackles the development of a new antimalarial agent with a fast clearance rate of asexual parasites and additional sexual blood stage activity against *Plasmodium falciparum* with a presumed novel mode-of-action.

Chlorotonil A is a highly lipohilic tricyclic macrolide consisting of an unusual gem-dichloro-1,3-dione moiety, a novel feature among natural polyketides. It is produced by the myxobacterium *Sorangium cellulosum*, a Gram-negative soil-dwelling bacterium. It showed very promising antiplasmodial activity in the low nanomolar range in a first screening, testing for in vitro activity against chloroquine-sensitive and chloroquine-resistant laboratory strains of *Plasmodium falciparum* (mean $IC_{50}$: 9 and 18 nM, respectively) and against clinical isolates from Gabon (median $IC_{50}$: 15.2 nM). It showed a very rapid onset of action in vitro; already after 1 h exposure and subsequent washing of the culture, the $IC_{50}$ was only 1.3-fold higher compared to the $IC_{50}$ when no washing step was applied. When tested for the inoculum effect, chlorotonil A showed nearly no variation in the $IC_{50}$ (1.2 fold difference between lowest and highest parasitemia) when assays were performed at starting parasitemia levels of 0.01, 0.05, 0.5 and 2.5%. Chloroquine and artesunate on the other hand showed a higher $IC_{50}$ when higher parasitemia levels were used (5.6-and 8.8-fold, respectively). So far, it was not possible to develop resistant parasites in vitro by drug pressure. Chlorotonil A showed very promising gametocytocidal activity against mature stage (stage IV-V) gametocytes in a bioluminescence assay measuring ATP. The obtained mean $IC_{50}$ was 29.6 nM displaying a superior activity to all other tested compounds in this assay, besides epoxomicin, which shows toxic effects in vivo. First in vivo experiments in mice showed that chlorotonil A is orally available and that it displays in vivo efficacy (4 day suppression test; activity >90% reduced parasitemia at different doses of 36-110 mg/kg in a pilot experiments). However, correct dosing in the mouse model was very difficult. The compound could only be given in solid form together with peanut butter, which hampers the ability to propose a correct and accurate dosing scheme.

Another natural derivative is chlorotonil B, resulting from the loss of one of the chlorine atoms with a keto-enol group. The tautomer B3, the 5-keto derivative, is obtained after silica gel purification of chlorotonil B (5-keto derivative from extract), and the other tautomer B1, the 3-keto derivative, is obtained after HPLC purification of chlorotonil B (5-keto derivative from extract).

The maximum tolerated concentration (MTC) of chlorotonil A and B through preliminary toxicity studies in zebrafish could not be determined because of observed precipitation in stock solutions and assay wells. Nonetheless, the MTC of more soluble epoxide derivatives (ChA-Epo2 and ChB-Epo) obtained through semi-synthesis as described below were determined, and showed that the chlorotonil B derivative is less toxic than the chlorotonil A derivative. Furthermore, MTC values for both are well above the $IC_{50}$ on *P. falciparum* and minimum inhibitory concentrations (MIC) on bacterial pathogens, resulting in selectivity indices in the range of 500 to 1000.

Chlorotonils show poor water solubility which limits their application and further development. Scaffold improvement cannot be achieved by total synthesis due to its lengthy 21 linear steps and low overall yield (1.5%), thus, efficient semi-synthetic routes were developed.

REFERENCES (1) Gerth K, Steinmetz H, Höfle G, Jansen R. Chlorotonil A, a macrolide with a unique gem-dichloro-1,3-dione functionality from *Sorangium cellulosum*, So ce1525. *Angew Chem Int Ed Engl* 2008, 47(3):600-602.

(2) Jungmann K, Jansen R, Gerth K, Huch V, Krug D, Fenical W, Müller R. Two of a Kind—The Biosynthetic Pathways of Chlorotonil and Anthracimycin. *ACS Chem Biol* 2015, 10(0:2480-2490.

(3) Held J, Gebru T, Kalesse M, Jansen R, Gerth K, Müller R, Mordmüller B. Antimalarial activity of the myxobacterial macrolide chlorotonil A. *Antimicrob Agents Chemother* 2014, 58(11):6378-6784.

(4) Rahn N, Kalesse M. The total synthesis of chlorotonil A. *Angew Chem Int Ed Engl* 2008, 47(3):597-599.

It was therefore an object of the present invention to provide new derivatives of the known chlorotonils which overcome the drawbacks of the state of the art.

The present invention provides compounds of general formula (I):

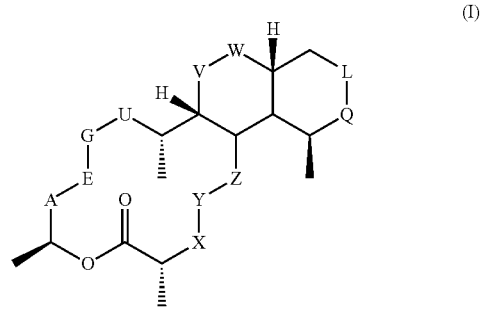

wherein
A-E together are a group of formula

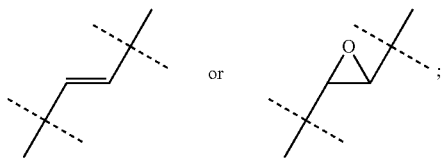

G-U together are a group of formula

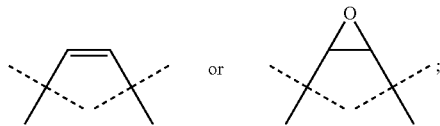

V-W together are a group of formula

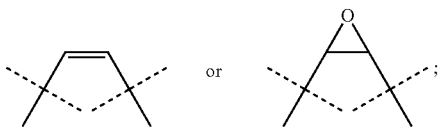

L-Q together are a group of formula

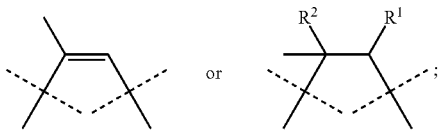

X-Y-Z together are a group of formula —C(=O)—C(Cl)$_2$—C(=O)—, —C(OH)=C(Cl)—C(=O)— or —C(=O)—C(Cl)=C(OH)—;

R$^1$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and R$^2$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or R$^1$ and R$^2$ together are a group of formula —O— (i.e. form an epoxide);

with the proviso that all of A-E, G-U, V-W and L-Q do not at the same time possess a double bond;

or a pharmaceutically acceptable salt, solvate or hydrate or a pharmaceutically acceptable formulation thereof.

The present invention moreover provides compounds of general formula (II):

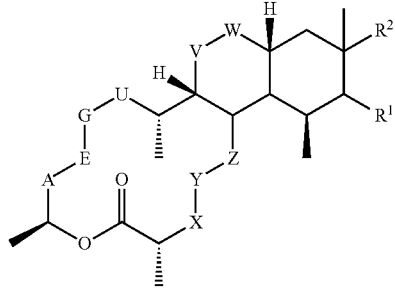

(II)

wherein
A-E together are a group of formula

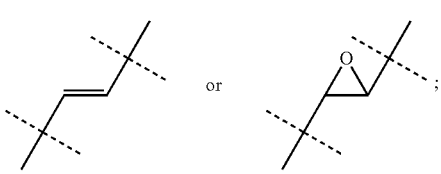

G-U together are a group of formula

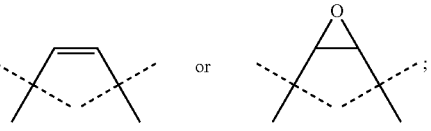

V-W together are a group of formula

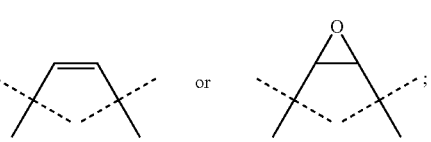

X-Y-Z together are a group of formula —C(=O)—C(Cl)$_2$—C(=O)—, —C(OH)=C(Cl)—C(=O)— or —C(=O)—C(Cl)=C(OH)—;

R$^1$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and R$^2$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or R$^1$ and R$^2$ together are a group of formula —O—;

or a pharmaceutically acceptable salt, solvate or hydrate or a pharmaceutically acceptable formulation thereof.

The present invention further provides compounds of general formula (III):

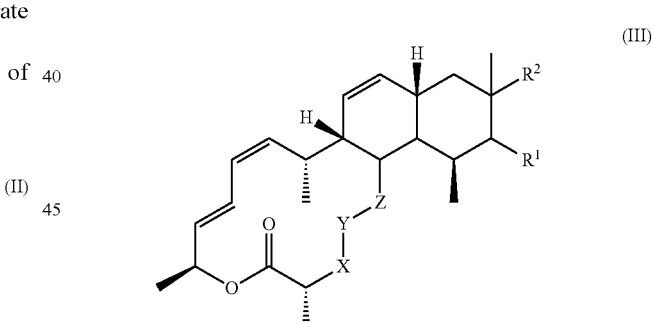

(III)

wherein
X-Y-Z together are a group of formula —C(=O)—C(Cl)$_2$—C(=O)—, —C(OH)=C(Cl)—C(=O)— or —C(=O)—C(Cl)=C(OH)—;

R$^1$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and R$^2$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or R$^1$ and R$^2$ together are a group of formula —O—;

or a pharmaceutically acceptable salt, solvate or hydrate or a pharmaceutically acceptable formulation thereof.

The present invention moreover provides compounds of general formula (IV):

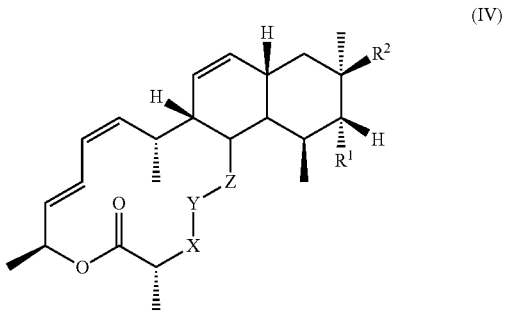

(IV)

wherein

X-Y-Z together are a group of formula —C(=O)—C(Cl)$_2$—C(=O)—, —C(OH)=C(Cl)—C(=O)— or —C(=O)—C(Cl)=C(OH)—;

R$^1$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and R$^2$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

or a pharmaceutically acceptable salt, solvate or hydrate or a pharmaceutically acceptable formulation thereof.

According to a preferred embodiment, at least one of R$^1$ and R$^2$ is OH (especially R$^2$).

According to a further preferred embodiment, R$^1$ and R$^2$ together are a group of formula —O— (i.e. form an epoxide).

Preferably, R$^1$ is a halogen atom, OH, ONO$_2$ or a group of formula —O—C$_{1-6}$ alkyl which group may be substituted by one or two hydroxy groups and/or by an optionally substituted phenyl group; and R$^2$ is OH.

Further preferably, R$^1$ is OH; and R$^2$ is a halogen atom, OH, ONO$_2$ or a group of formula —O—C$_{1-6}$ alkyl which group may be substituted by one or two hydroxy groups and/or by an optionally substituted phenyl group.

Moreover preferably, R$^1$ is F, Cl, Br, OH, ONO$_2$, OMe, OEt, OBu, OBuOH, Oisoamyl, OBn or glycerol; and R$^2$ is OH.

Further preferably, R$^1$ is OH and R$^2$ is Cl, OMe or OEt.

Moreover preferably, Z is —C(=O)— and X-Y together are a group of formula —C(=O)—C(Cl)$_2$— or —C(OH)=C(Cl)—.

Especially preferred are compounds of formula (V):

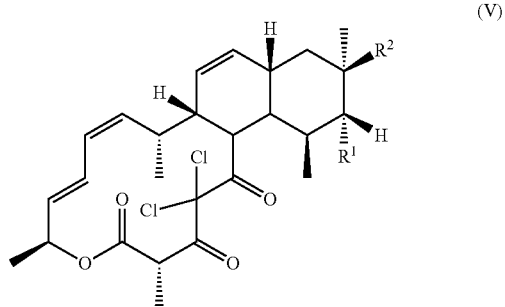

(V)

wherein R$^1$ and R$^2$ are as defined above, or a pharmaceutically acceptable salt, solvate or hydrate or a pharmaceutically acceptable formulation thereof.

Moreover especially preferred are compounds of formula (VI):

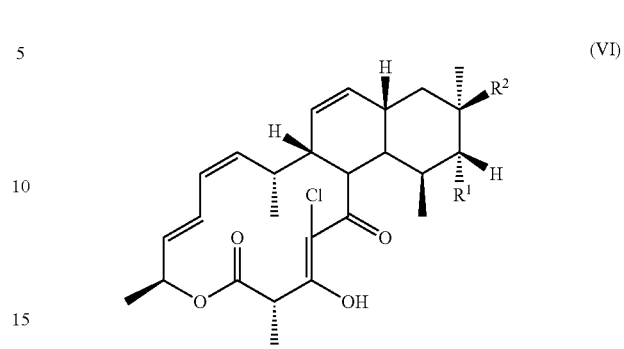

(VI)

wherein R$^1$ and R$^2$ are as defined above, or a pharmaceutically acceptable salt, solvate or hydrate or a pharmaceutically acceptable formulation thereof.

Moreover especially preferred are compounds of formula (VII):

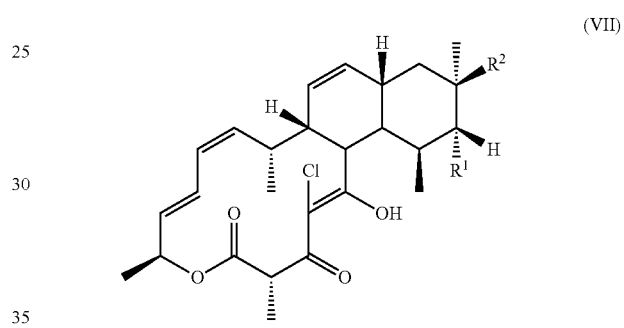

(VII)

wherein R$^1$ and R$^2$ are as defined above, or a pharmaceutically acceptable salt, solvate or hydrate or a pharmaceutically acceptable formulation thereof.

Preferred are compounds of formula (V), (VI) and (VII), wherein R$^2$ is OH.

Further especially preferred are the following compounds:

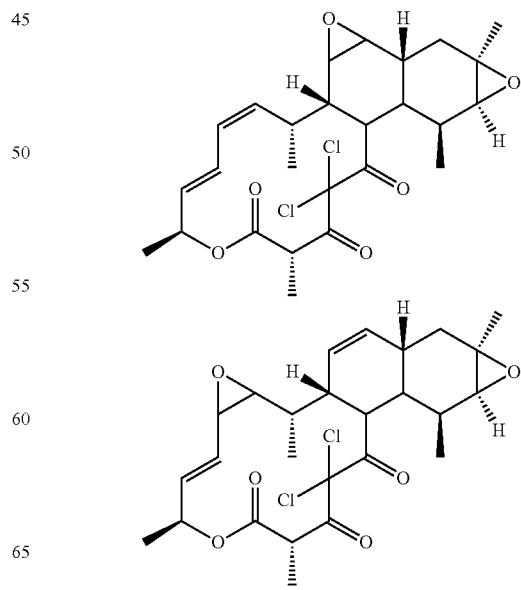

-continued

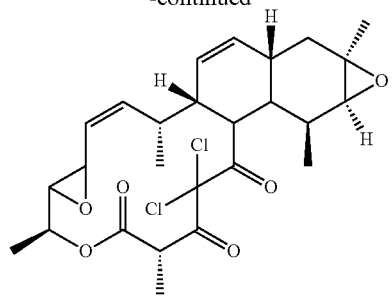

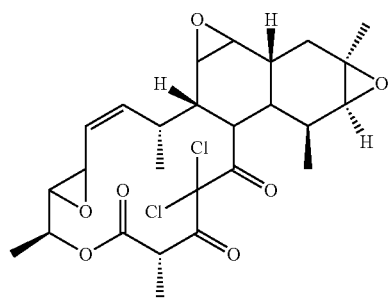

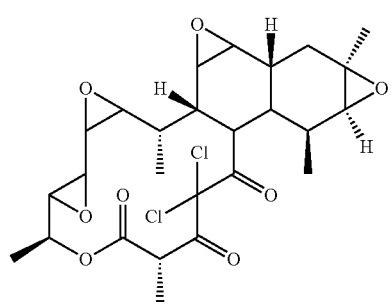

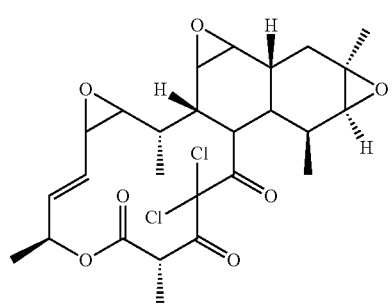

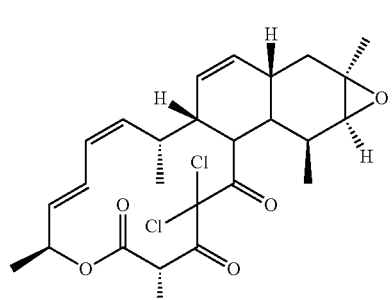

or a pharmaceutically acceptable salt, solvate or hydrate or a pharmaceutically acceptable formulation thereof.

Moreover especially preferred are the following compounds:

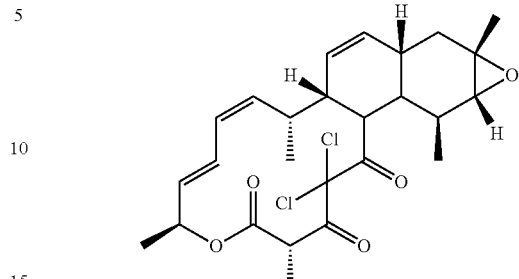

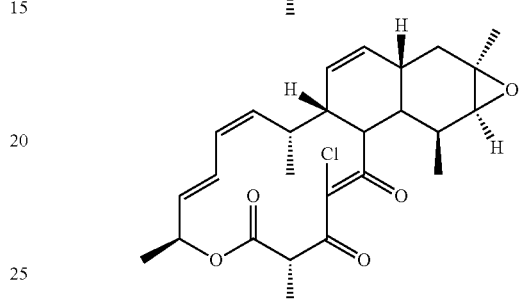

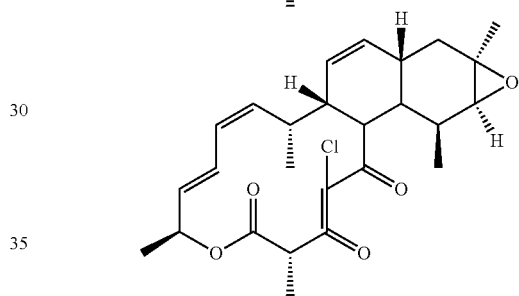

or a pharmaceutically acceptable salt, solvate or hydrate or a pharmaceutically acceptable formulation thereof.

Especially preferred are the compounds disclosed in the examples or a pharmaceutically acceptable salt, solvate or hydrate or a pharmaceutically acceptable formulation thereof.

The expression alkyl refers to a saturated, straight-chain or branched hydrocarbon group that contains from 1 to 20 carbon atoms, preferably from 1 to 15 carbon atoms, especially from 1 to 10 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expression $C_{1-6}$ alkyl refers to a saturated, straight-chain or branched hydrocarbon group that contains from 1 to 6 carbon atoms. The expression $C_{1-4}$ alkyl refers to a saturated, straight-chain or branched hydrocarbon group that contains from 1 to 4 carbon atoms. Examples are a methyl (Me), $CF_3$, ethyl, propyl, iso-propyl, n-butyl, iso-butyl, sec-butyl or tert-butyl group.

The expressions alkenyl and alkynyl refer to at least partially unsaturated, straight-chain or branched hydrocarbon groups that contain from 2 to 20 carbon atoms, preferably from 2 to 15 carbon atoms, especially from 2 to 10 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1 to 8; especially preferably 1, 2, 3 or 4) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 8 heteroatoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Especially preferably, the expression heteroalkyl refers to an alkyl group as defined above (straight-chain or branched) in which one or more (preferably 1 to 6; especially preferably 1, 2, 3 or 4) carbon atoms have been replaced by an oxygen, sulfur or nitrogen atom; this group preferably contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen); this group may preferably be substituted by one or more (preferably 1 to 6; especially preferably 1, 2, 3 or 4) fluorine, chlorine, bromine or iodine atoms or OH, =O, SH, =S, $NH_2$, =NH, $N_3$, CN or $NO_2$ groups.

Examples of heteroalkyl groups are groups of formulae: $R^a$—O—$Y^a$—, $R^a$—S—$Y^a$—, $R^a$—SO—$Y^a$—, $R^a$—$SO_2$—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, —$SO_2Me$, —COOH, —$NHCONH_2$, —NHAc, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile (—CN), isonitrile, cyanate, thiocyanate, isocyanate, isothiocyanate and alkylnitrile groups.

The expression alkylene group refers to a divalent alkyl group; the expression alkenylene group refers to a divalent alkenyl group (e.g. a group of formula —CH=C($CH_3$)—); and the expression heteroalkylene group refers to a divalent heteroalkyl group (e.g. a group of formula —O—CH($CH_3$)— or —CO—O—$CH_2$—).

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10

(especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, 4-hydroxypyridyl (4-pyridonyl), 3,4-hydroxypyridyl (3,4-pyridonyl), oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (especially 1 or 2 rings), each containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to groups containing both aryl and/or heteroaryl groups and also alkyl, alkenyl, alkynyl and/or heteroalkyl and/or cycloalkyl and/or heterocycloalkyl groups in accordance with the above definitions. A heteroalkyl group preferably contains one or two aromatic ring systems (especially 1 or 2 rings), each containing from 5 or 6 to 9 or 10 ring carbon atoms and one or two alkyl, alkenyl and/or alkynyl groups containing 1 or 2 to 6 carbon atoms and/or one or two heteroalkyl groups containing 1 to 6 carbon atoms and 1, 2 or 3 heteroatoms selected from O, S and N and/or one or two cycloalkyl groups each containing 5 or 6 ring carbon atoms and/or one or two heterocycloalkyl groups, each containing 5 or 6 ring atoms comprising 1, 2, 3 or 4 oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, phthalidyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The expression "optionally substituted" especially refers to groups that are optionally substituted by fluorine, chlorine, bromine or iodine atoms or by OH, =O, SH, =S, $NH_2$, =NH, $N_3$ or $NO_2$ groups. This expression refers furthermore especially to groups that may be substituted by one, two, three or more (preferably unsubstituted) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more (preferably unsubstituted) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

Preferred substituents are: halogen atoms (e.g. F, Cl, Br), groups of formula —OH, —O—$C_{1-6}$ alkyl (e.g. —OMe, —OEt, —O-nPr, —O-iPr, —O-nBu, —O-iBu or —O-tBu), —$NH_2$, —NH$C_{1-6}$ alkyl, —N($C_{1-6}$ alkyl)$_2$, —COOH, COO$C_{1-6}$ alkyl, COC$_{1-6}$ alkyl, —$SO_3H$, =O, —$SO_2NH_2$, —$CONH_2$, CONH$C_{1-6}$ alkyl, CON($C_{1-6}$ alkyl)$_2$, —CN, —$C_{1-6}$ alkyl (e.g. -Me, -Et, -nPr, -iPr, -nBu, -iBu, -tBu or —$CF_3$), —SH, —S—$C_{1-6}$ alkyl, NHAc, —$NO_2$, —$NHCONH_2$, —$SO_2Me$, and cyclopropyl.

The term halogen refers to F, Cl, Br or I.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may independently of each other optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Owing to their substitution, the compounds of the present invention may contain one or more centers of chirality. The present invention therefore includes both all pure enantiomers and all pure diastereoisomers and also mixtures thereof in any mixing ratio. The present invention moreover also includes all cis/trans-isomers of the compounds of the present invention and also mixtures thereof. The present invention moreover includes all tautomeric forms of the compounds of the present invention.

The present invention further provides pharmaceutical compositions comprising one or more compounds described herein or a pharmaceutically acceptable salt, solvate or hydrate thereof, optionally in combination with one or more carrier substances and/or one or more adjuvants.

The present invention furthermore provides compounds or pharmaceutical compositions as described herein for use in the treatment and/or prophylaxis of bacterial infections.

The present invention furthermore provides compounds or pharmaceutical compositions as described herein for use in the treatment and/or prophylaxis of malaria.

It is a further object of the present invention to provide a compound as described herein or a pharmaceutical composition as defined herein for the preparation of a medicament for the treatment and/or prophylaxis of bacterial infections.

It is a further object of the present invention to provide a compound as described herein or a pharmaceutical composition as defined herein for the preparation of a medicament for the treatment and/or prophylaxis of malaria.

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein.

The compounds described herein may be solvated, especially hydrated. The hydratization/hydration may occur during the process of production or as a consequence of the hygroscopic nature of the initially water free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

The pharmaceutical compositions according to the present invention comprise at least one compound described herein and, optionally, one or more carrier substances and/or adjuvants.

As mentioned above, therapeutically useful agents that contain compounds described herein, their solvates, salts or formulations are also comprised in the scope of the present invention. In general, the compounds described herein will be administered by using the known and acceptable modes known in the art, either alone or in combination with any other therapeutic agent.

For administration, such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, and polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

EXAMPLES

Activity Testing
Antimicrobial Assay:

Bacterial strains used in susceptibility assays (minimum inhibitory concentrations, MIC) were either part of our internal strain collection or were purchased form the German Collection of Microorganisms and Cell Cultures (DSMZ). All compounds were prepared as DMSO stocks and MIC values were determined in standard microbroth dilution assays. Overnight cultures of bacteria were diluted in cation-adjusted Muller-Hinton broth (BBL™, BD) and were adjusted to approximately $10^5$ cfu/mL. For the *E. coli* culture, 3 µg/mL of polymyxin B nonapeptide (PMBN) was added to increase permeability of the outer membrane as chlorotonils were previously shown to not penetrate into Gram-negative cells. Bacteria were grown in the presence of the derivatives in serial dilution for 16 h at their optimal growth temperature. MIC values were determined according to CLSI guidelines (antibiotic concentration at which no visible bacterial growth is observed).

Cytotoxicity Assay

The murine fibroblast cell line L-929 was obtained from the German Collection of Microorganisms and Cell Cultures (DSMZ) and maintained under conditions recommended by the depositor. Cells were seeded at $6\times10^3$ cells per well of sterile 96-well plates in 180 μL complete medium and treated with the compounds in serial dilution after 2 h of equilibration. After 5 d, viability was assessed by the MTT method. After 1.5 h incubation with 0.5 mg/mL MTT reagent, cells were washed with PBS and 100 μL of 2-propanol/10 N HCl (250:1) was added. The absorbance at 570 nm was determined on a microplate reader and cell viability was expressed as percentage relative to the respective solvent control. Half-inhibitory concentrations ($IC_{50}$) were determined by sigmoidal curve fitting.

Antiplasmodial Assay

Parasite Culture:

Two laboratory strains of *P. falciparum*, the chloroquine sensitive 3D7 and the multi-resistant Dd2 were kept in continuous culture as previously described (Trager and Jensen 1976). In brief, parasites were kept in complete culture medium (RPMI 1640, 25 mM HEPES, 2 mM L-glutamine, 50 μg/ml gentamicin and 0.5% w/v AlbuMAX) at 37° C., 5% $CO_2$ and 5% oxygen at 5% hematocrit with daily change of medium. Synchronization was performed with sorbitol twice a week (Lambros and Vanderberg 1979).

In Vitro Drug Sensitivity Assay

All compounds were dissolved in DMSO at stock dilutions between 25 and 100 mM; the reference drug chloroquine diphosphate (MW: 515.86) was diluted in distilled water and DMSO, respectively. Further dilutions were prepared in complete culture medium so that final concentrations of solvent did not interfere with parasite growth. Antiplasmodial activity of the different compounds was tested in a drug sensitivity assay against the two laboratory strains using the histidine-rich protein 2 (HRP2) assay as described previously (Noedl 2005). In brief: 96 well plates were pre-coated with the different compounds in a threefold dilution before ring stage parasites were added in complete culture medium at a hematocrit of 1.5% and a parasitemia of 0.05% in a total volume of 225 μl per well. After three days of incubation plates were frozen until analyzed by HRP2-ELISA. All compounds were evaluated in duplicate in at least two independent experiments. The 50% inhibitory concentrations ($IC_{50}$) were determined by analysing the nonlinear regression of log concentration—response curves using the drc-package v0.9.0 of R v2.6.1 (Vienna Austria 2008).

Zebrafish Embryo Toxicity

The maximum tolerated concentration (MTC) was determined on zebrafish larvae of the AB wildtype line and the TLF wild type line. Larvae were placed into a 96-well plate (one larva per well) and incubated in a solution at different concentrations (100, 50, 25, 10, 1 μM) of ChA, ChA-Epo2, ChB or ChB-Epo at two days post fertilization (dpf) for AB and in a solution at different concentrations of ChA (100, 50 μM) ChA-Epo2 (25, 10, 1 μM), ChB (100, 50 μM) or ChB-Epo (100, 50, 25 μM) at one dpf for TLF. Five zebrafish larvae were used per condition. The incubated embryos were kept in compound solutions at 28° C. until five dpf and monitored daily by microscopy. The final MTC result was recorded at five dpf. Compound solutions were prepared in the larvae medium Danieau's. Additionally a solution of 0.5% DMSO in Danieau's was used as vehicle control and Danieau's alone as a negative control.

REFERENCES

Lambros, C. and J. P. Vanderberg (1979). "Synchronization of Plasmodium falciparum erythrocytic stages in culture." *J Parasitol* 65(3): 418-20.

Trager, W. and J. B. Jensen (1976). "Human malaria parasites in continuous culture." *Science* 193(4254): 673-5.

Noedl, H., J. Bronnert, et al. (2005). "Simple histidine-rich protein 2 double-site sandwich enzyme-linked immunosorbent assay for use in malaria drug sensitivity testing." *Antimicrob Agents Chemother* 49(8): 3575-7.

Vienna Austria R Foundation for Statistical Computing. 2008. R: A Language and Environment for Statistical Computing. R Foundation for Statistical Computing 1:26673.

Determination of Water Solubility

Method 1:

10 mg of compound was suspended in 1 L of tap water and the solution was stirred at room temperature for 18 h. Upon completion, solution was sonicated for another hour, centrifuged and the supernatant was separated from the precipitate. Both aliquots were lyophilized, and weighed. This procedure was performed in triplicates.

Method 2:

A standard curve with 10 calibration points of the compound of interest is plotted using HPLC-MS and serial dilution. The dilutions and stock solutions were prepared in THF as a solvent. Following the measurements, a saturated solution in water of the compound in study was also measured. Upon plotting the standard curve using the peak areas of the MS peaks, the water samples were plotted along the curve and the solubility was then calculated.

Detailed NMR Conditions

All 1D ($^1$H and $^{13}$C) and 2D (COSY, ROESY, HSQC-DEPT and HMBC) NMR spectra were recorded on a Bruker Ascend 700 spectrometer with a 5 mm TXI cryoprobe (1H at 700 MHz, 13C at 175 MHz). 2D Experiments were recorded using standard pulse programs. The samples were dissolved in $CDCl_3$ and the chemical shifts of the solvent signals at 7.26 ppm (δH) and 77.16 ppm (δC) were considered as internal standard (reference signal). The observed chemical shift (δ) values are given in ppm and the coupling constants (J) in Hz. For ROESY experiments measurements were carried out with mixing times of 400 ms.

Detailed LCMS and LCMSMS Conditions

The measurements to detect all chlorotonil derivatives were performed on a Dionex Ultimate 3000 RSLC system using a BEH C18, 50×2.1 mm, 1.7 μm dp column (Waters, Germany). Separation of 1 μl sample was achieved by a linear gradient from (A) $H_2O$+0.1% FA to (B) ACN+0.1% FA at a flow rate of 600 μL/min and 45° C. The gradient was initiated by a 0.5 min isocratic step at 5% B, followed by an increase to 95% B in 6 min to end up with a 2 min step at 95 B before re-equilibration under the initial conditions. UV spectra were recorded by a DAD in the range from 200 to 600 nm. The LC flow was split to 75 μL/min before entering the maXis 4G hr-ToF mass spectrometer (Bruker Daltonics, Germany) using the Apollo ESI source. Mass spectra were acquired in centroid mode ranging from 150-2500 m/z at a 2 Hz scan rate. Settings for MS/MS measurements were: minimum precursor intensity is set to 10000. Full scan spectra are acquired at 2 Hz followed by MS/MS spectra acquisition at variable scan speed ranging from 1 to 3 Hz, as a function of precursor intensity. CID energy varies linearly from 30, 35, 45, to 55 eV with respect to the precursor m/z from 300, 600, 1000, to 2000 m/z. The collision cell is set to ramp collision energy (80-120% of the set value with equal weights of both values), collision RF (700 to 1000 Vpp with equal weights of both values) and transfer time (90-110 μs) for every MS/MS scan. The number of precursors was set to 2 and precursors were moved to an exclusion list for 0.2 min after two spectra were measured (typical chromatographic peak width was 0.10-0.15 min). Precursors were reconsidered if their intensity changed fivefold.

Syntheses

Chemical structures of natural chlorotonils A and B and the chlorotonil derivatives of the present invention:

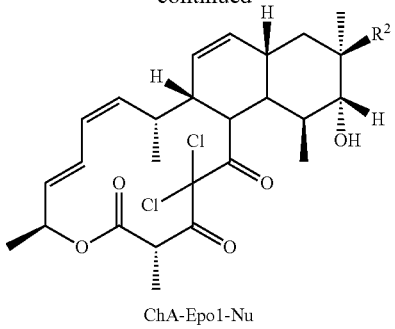
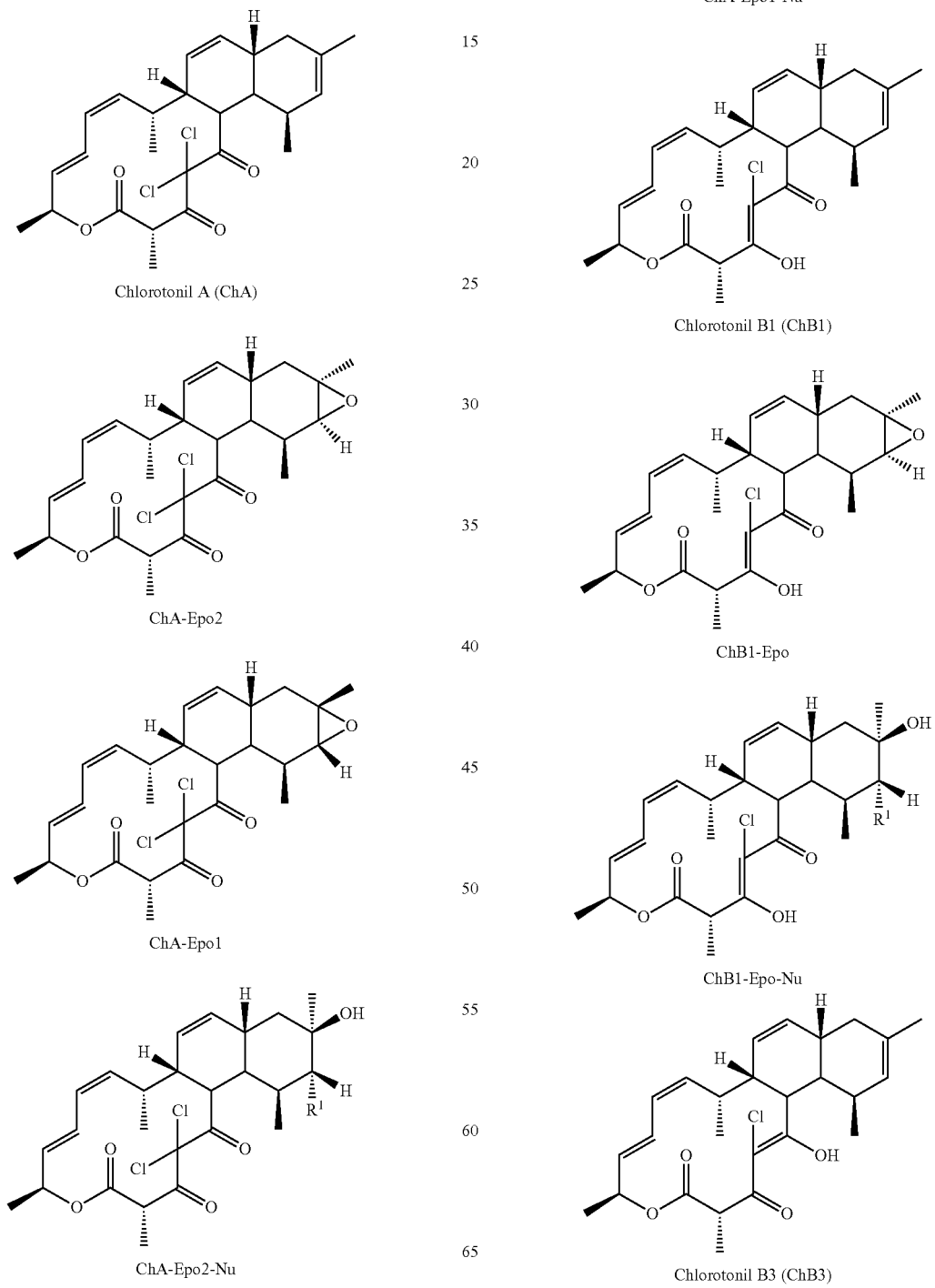

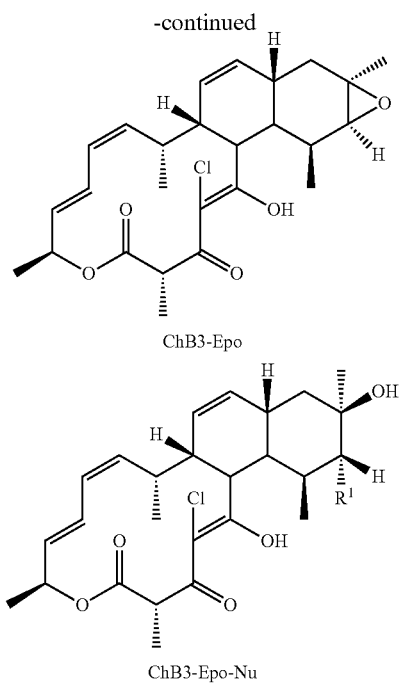

ChB3-Epo

ChB3-Epo-Nu

Ch-A-Epo:

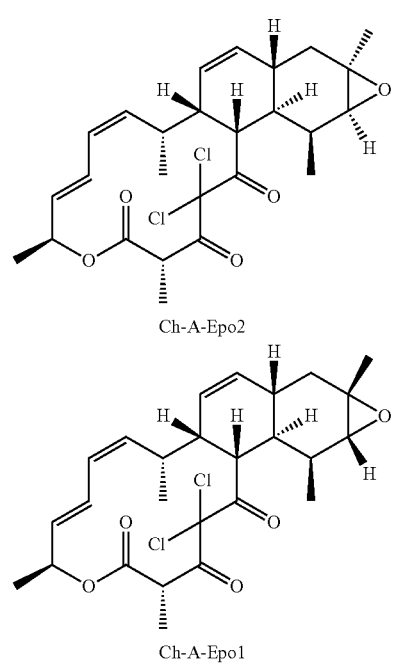

Ch-A-Epo2

Ch-A-Epo1

Chlorotonil A (0.21 mmol, 100 mg) was dissolved in chloroform (10 ml) and meta-Chloroperoxybenzoic acid (m-CPBA) (0.252 mmol, 43.35 mg) in chloroform (5 ml) was added to the solution dropwise over 30 min. The mixture was left stirring at room temperature for 16 hours. When no trace of starting material was observed (TLC: silica, $CHCl_3$:DCM, 1:1, UV, $R_f$), the solution was concentrated under reduced pressure and the mixture was purified using flash chromatography (silica, $CHCl_3$:DCM, 1:1, UV) to yield Ch-A-Epo1 (0.03 mmol, 15.6 mg, 15% yield) and Ch-A-Epo2 (0.17 mmol, 83.2 mg, 80% yield) both as white powder. HRMS (ESI, +ve) $C_{26}H_{32}Cl_2O_5$ $[M+H]^+$ calculated for 495.1700, found 495.1702.

NMR-Data of Ch-A-Epo 1:

Ch-A-Epo1

| H | $\delta_H$ | m | J(Hz) | COSY | ROESY | C | $\delta_C$ | HMBC |
|---|---|---|---|---|---|---|---|---|
| — | | | | | — | 1 | 168.0 | |
| 2 | 4.53 | q | 7.0 | 23 | — | 2 | 47.1 | 23, 1, 3 |
| — | | | | | | 3 | 192.0 | |
| — | | | | | | 4 | 81.4 | |
| — | | | | | | 5 | 196.0 | |
| 6 | 3.70 | dd | 12.2, 6.6 | 7, 15 | 15 | 6 | 49.3 | 12, 16, 7, 8, 15, 5, 13, 14 |
| 7 | 2.17 | td | 10.8, 4.2 | 6, 8, | 8, 24/26 | 7 | 31.5 | 6, 9, 12, 24, 11, 15, 5 |
| 8 | 2.45 | 13 | 2.3 | 9, 7, 24/26, 25 | 9 | 8 | 29.0 | 9, 10, 12, 24, 16 |
| 9 | 2.83 | d | 1.7 | 8, 11α, 25 | 8, 25, 15 | 9 | 65.6 | 10, 24, 8, 6, 12 |
| — | | | | | — | 10 | 57.4 | |
| 11α | 1.59 | t | 13.1 | 9, 7, 12/11β | 12, 7 | 11 | 36.5 | 9, 10, 7, 12, 13 |
| 11β | 1.93-2.01 | m | | | | — | | |
| 12 | 1.93-2.01 | m | | | | 12 | 28.6 | |
| 13 | 5.55-5.59 | m | | | | 13 | 132.2 | |
| 14 | 5.46-5.52 | m | | | | 14 | 124.2 | |
| 15 | 2.98 | m | 2.1 | 16, 6, 13, 14, 12/11β | 6 | 15 | 42.7 | 6, 7, 9, 13, 14, 16, 17, 26 |
| 16 | 2.71-2.77 | m | | 17, 24/26, 15 | 15, 7 | 16 | 33.4 | 6, 13, 14, 15, 19, 18, 26 |
| 17 | 5.28 | t | 9.1 | 16, 18, 19 | 18, 14/20 13/21 | 17 | 139.3 | 15, 16, 18, 19, 26, 21 |
| 18 | 5.86 | t | 10.9 | 19, 17 | 19, 17, 14/20 13/21 | 18 | 125.6 | 16, 15, 19, 20, 21 |
| 19 | 6.03 | td | 11.5, 1.3 | 18, 20, 17, 21 | 18, 14/20, 17, 16 | 19 | 124.0 | 17, 18, 20, 21, 22 |
| 20 | 5.46-5.52 | m | | | | 20 | 130.4 | |
| 21 | 5.55-5.59 | m | | | — | 21 | 70.4 | |
| 22 | 1.35 | d | 6.7 | 21/14 | 13/21, 14/20 | 22 | 21.1 | 20, 19, 21 |
| 23 | 1.65 | d | 7.0 | 2 | 2 | 23 | 17.1 | 3, 1, 2 |
| 24 | 0.91-0.93 | m | | | | 24 | 10.4 | |
| 25 | 1.27 | s | | | 9, 12/11β, 11α | 25 | 24.7 | 9, 10, 11 |
| 26 | 0.91-0.93 | m | | | | 26 | 15.8 | |

NMR-Data of Ch-A-Epo2:

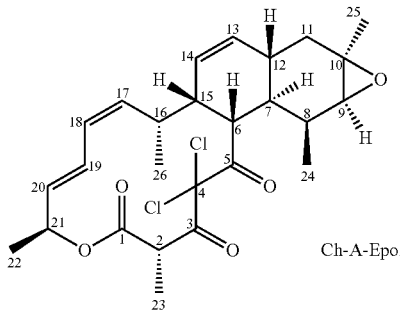

Ch-A-Epo2

| H | $\delta_H$ | m | J(Hz) | COSY | ROESY | C | $\delta_C$ | HMBC |
|---|---|---|---|---|---|---|---|---|
| — | | | | | — | 1 | 168.0 | |
| 2 | 4.54 | q | 7.0 | 23 | — | 2 | 47.2 | 23, 1, 3 |
| — | | | | | | 3 | 191.8 | |
| — | | | | | | 4 | 81.4 | |
| — | | | | | | 5 | 197.7 | |
| 6 | 3.66 | dd | 12.0, 6.5 | 7, 15 | 15 | 6 | 48.7 | 12, 16, 7, 8, 15, 5, 13, 14 |
| 7 | 1.97 | td | 11.2, 5.5 | 6, 8, | 8, 24/26 | 7 | 37.0 | 6, 9, 12, 24, 11, 15, 5 |
| 8 | 2.34 | 6 | 6.2 | 9, 7, 24/26, 25 | 9 | 8 | 27.8 | 9, 10, 12, 24, 16 |
| 9 | 3.06 | d | 5.6 | 8 | 8, 25, 15 | 9 | 64.5 | 10, 24, 8, 6, 12 |
| — | | | | | — | 10 | 59.2 | |
| 11α | 1.41 | t | 8.6 | 9, 7, 12/11β | 12, 7 | 11 | 39.1 | 9, 10, 7, 12, 13 |
| 11β | 2.11 | dd | 14.1, 3.6 | | — | | | |
| 12 | 2.04-2.07 | m | | | | 12 | 27.9 | |
| 13 | 5.60 | App d | 9.6 | | | 13 | 132.7 | |
| 14 | 5.47 | ddd | 4.8, 2.3 | | | 14 | 123.7 | |
| 15 | 2.98-3.01 | m | | | 6 | 15 | 42.4 | 6, 7, 9, 13, 14, 16, 17, 26 |
| 16 | 2.74-2.79 | m | | 17, 24/26, 15 | 15, 7 | 16 | 33.3 | 6, 13, 14, 15, 19, 18, 26 |
| 17 | 5.25 | t | 9.3 | 16, 18, 19 | 18, 14/20 13/21 | 17 | 139.0 | 15, 16, 18, 19, 26, 21 |
| 18 | 5.86 | t | 10.9 | 19, 17 | 19, 17, 14/20 13/21 | 18 | 125.6 | 16, 15, 19, 20, 21 |
| 19 | 5.99-6.03 | m | | 18, 20, 17, 21 | 18, 14/20, 17, 16 | 19 | 123.7 | 17, 18, 20, 21, 22 |
| 20 | 5.51 | dd | 15.3, 1.9 | | | 20 | 130.4 | |
| 21 | 5.60 | App d | 9.6 | | — | 21 | 70.4 | |
| 22 | 1.31 | d | 6.7 | 21/14 | 13/21, 14/20 | 22 | 21.0 | 20, 19, 21 |
| 23 | 1.65 | d | 7.0 | 2 | 2 | 23 | 17.2 | 3, 1, 2 |
| 24 | 0.93 | App d | 6.6 | | | 24 | 9.7 | |
| 25 | 1.35 | s | | | 9, 12/11β, 11α | 25 | 23.1 | 9, 10, 11 |
| 26 | 0.93 | App d | 6.6 | | | 26 | 15.7 | |

Ch-B-Epo:

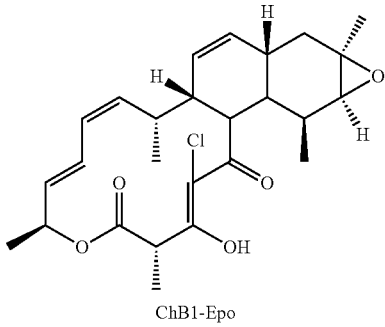

ChB1-Epo

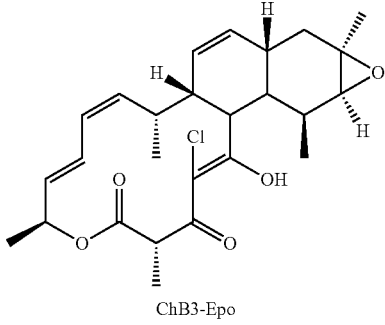

ChB3-Epo

Ch-B1-Epo and Ch-B3-Epo (0.018 mmol, 8.3 mg, 80% yield, 15:85 ratio) as white powder were prepared from ChB3 following the same procedure described above for Ch-A-Epo. (TLC:silica, CHCl$_3$:DCM, 1:1, UV, R$_f$). HRMS (ESI, +ve) C$_{26}$H$_{33}$ClO$_5$ [M+H]$^+$ calculated for 461.2089, found 461.2087.

NMR-Data of ChB1-Epo:

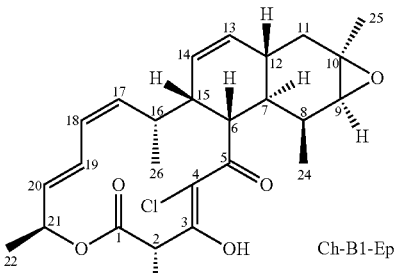

Ch-B1-Epo

| H | $\delta_H$ | m | J(Hz) | COSY | C | $\delta_C$ | HMBC |
|---|---|---|---|---|---|---|---|
| — | | | | | 1 | 168.2 | — |
| 2 | 4.38 | q | 7.0 | 23 | 2 | 44.8 | 23, 1, 3 |
| — | | | | | 3 | 187.8 | — |
| — | | | | | 4 | 109.2 | — |
| — | | | | | 5 | 194.2 | — |
| 6 | 3.34 | dd | 12.3, 6.5 | 7, 15 | 6 | 45.7 | 5, 4, 15, 7, 16, 8 |
| 7 | 1.94 | td | 17.4, 5.9 | 6, 8 12/11α | 7 | 36.0 | 24, 8, 11, 15, 6, 5 |
| 8 | 2.44-2.52 | m | | 9, 7, 24 | 8 | 28.4 | 24, 7, 9, 12 |
| 9 | 3.03 | d | 5.4 | 8 | 9 | 64.7 | 10, 7, 8, 25 |
| — | | | | | 10 | 59.3 | — |
| 11α | 2.05-2.16 | m | | 11β | 11 | 38.7 | 12, 7, 10, 9, 13 |
| 11β | 1.38-1.46 | m | | 12/11α | | | 12, 7, 10, 9, 13 |
| 12 | 2.05-2.16 | m | | 11β | 12 | 28.5 | 7, 10, 13 |

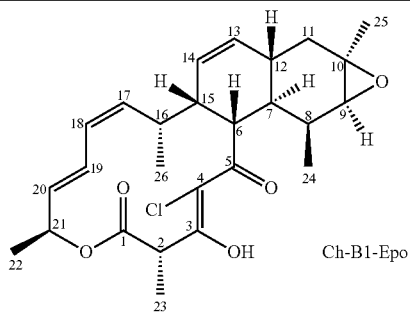

Ch-B1-Epo

| H | δ_H | m | J(Hz) | COSY | C | δ_C | HMBC |
|---|---|---|---|---|---|---|---|
| 13 | 5.62 | d | 10.0 | 14, 11β 12/11α | 13 | 132.7 | 15, 11a, 7, 12, 14 |
| 14 | 5.51 | ddd | 10.1, 4.6, 2.1 | 13, 15 | 14 | 124.4 | 13, 12, 15 |
| 15 | 2.73-2.80 | m |  | 14, 6, 12 | 15 | 42.1 | 14, 13 |
| 16 | 2.52-2.60 | m |  | 17, 26, 18, 15 | 16 | 33.0 | 15, 26, 17, 14, 18 |
| 17 | 5.37 | t | 9.6 | 16, 18 | 17 | 138.7 | 15, 16, 19, 26, 21 |
| 18 | 5.88 | t | 10.8 | 19, 17 | 18 | 126.0 | 16, 15, 19, 20 |
| 19 | 6.32 | t | 13.4 | 18, 20 | 19 | 123.3 | 17, 18, 20, 21 |
| 20 | 5.55 | dd | 15.2, 2.1 | 21, 19 | 20 | 131.7 | 21, 18 |
| 21 | 5.43-5.49 | m |  | 22, 20 | 21 | 70.5 | 22, 19 |
| 22 | 1.35 | d | 6.1 | 21 | 22 | 20.8 | 20, 21 |
| 23 | 1.44 | d | 6.9 | 2 | 23 | 12.1 | 3, 1, 2 |
| 24 | 0.85 | d | 7.1 | 8 | 24 | 10.2 | 9, 8, 7 |
| 25 | 1.34 | s |  |  | 25 | 23.0 | 9, 10, 11 |
| 26 | 0.94 | d | 6.6 | 16 | 26 | 16.8 | 16, 15, 17 |

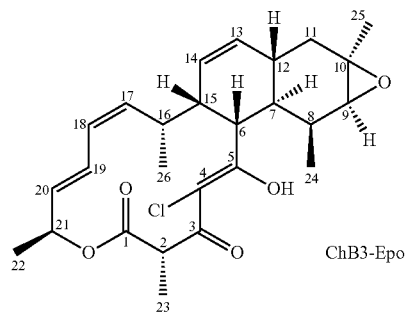

ChB3-Epo

| H | δ_H | m | J(Hz) | COSY | C | δ_C | HMBC |
|---|---|---|---|---|---|---|---|
|  |  |  |  |  | 1 | 175.1 | — |
| 2 | 4.58 | q | 6.9 | 23 | 2 | 46.1 | 23, 1, 3 |
|  |  |  |  |  | 3 | 180.9 | — |
|  |  |  |  |  | 4 | 107.7 | — |
|  |  |  |  |  | 5 | 193.9 | — |
| 6 | 3.29 | dd | 12.0, 7.0 | 7, 15 | 6 | 47.4 | 5, 15, 7, 16, 8 |
| 7 | 1.81 | td | 16.7, 6.1 | 6, 8, 12/11α | 7 | 36.5 | 24, 8, 11, 15, 6 |
| 8 | 2.78-2.85 | m |  | 9, 7, 24 | 8 | 28.8 | 24, 7, 12 |
| 9 | 2.99 | d | 5.3 | 8 | 9 | 65.0 | 10, 7, 8, 25 |
|  |  |  |  |  | 10 | 59.4 | — |
| 11α | 1.99-2.14 | m |  | 11β | 11 | 39.0 | 12, 7, 10, 9, 13 |
| 11β | 1.38-1.46 | m |  | 12/11α |  |  | 12, 7, 10, 9, 13 |
| 12 | 1.99-2.14 | m |  | 11β | 12 | 28.7 | 7, 10, 13 |
| 13 | 5.53-5.58 | m |  | 14, 15, 11β 12/11α | 13 | 132.8 | 15, 12, 14 |

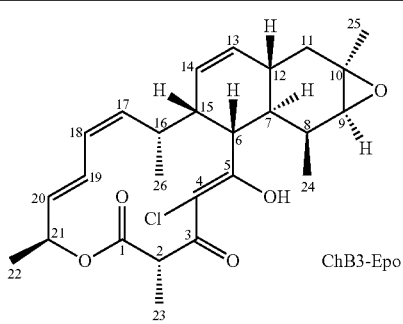

ChB3-Epo

| H | δ_H | m | J(Hz) | COSY | C | δ_C | HMBC |
|---|---|---|---|---|---|---|---|
| 14 | 5.46 | ddd | 10.0, 4.3, 2.3 | 13, 15 | 14 | 125.0 |  |
| 15 | 2.87-2.94 | m |  | 14, 6 | 15 | 41.3 |  |
| 16 | 2.31-2.41 | m |  | 17, 26, 15 | 16 | 33.6 | 15, 26, 17, 14, 18 |
| 17 | 5.32 | t | 10.0 | 16, 18 | 17 | 139.0 | 15, 16, 19, 26, 21 |
| 18 | 5.79 | t | 10.7 | 19, 17 | 18 | 125.7 | 16, 15, 19, 20, 17, 21 |
| 19 | 6.13 | t | 13.2 | 18, 20 | 19 | 124.1 | 17, 18, 20, 21 |
| 20 | 5.43 | dd | 15.4, 1.8 | 21, 19 | 20 | 131.1 | 22, 21, 18 |
| 21 | 5.58-5.64 | m |  | 22, 20 | 21 | 69.6 | 22, 19 |
| 22 | 1.35 | d | 6.6 | 21 | 22 | 20.6 | 20, 21 |
| 23 | 0.98 | d | 7.0 | 2 | 23 | 14.6 | 3, 1, 2 |
| 24 | 0.81 | d | 7.1 | 8 | 24 | 11.0 | 9, 8, 7 |
| 25 | 1.29 | s |  |  | 25 | 23.7 | 9, 10, 11 |
| 26 | 0.73 | d | 6.5 | 16 | 26 | 16.6 | 16, 15, 17 |

Ch-A-Epo 1-OMe:

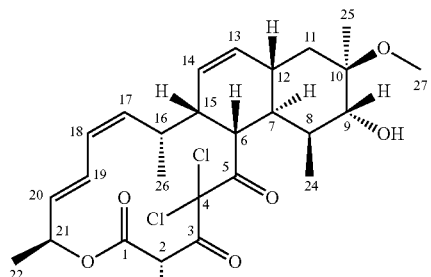

Ch-A-Epo1-OMe

Ch-A-Epo1 (0.01 mmol, 5 mg) was dissolved in methanol (2 ml) and concentrated sulfuric acid (99.99%, 50 μL) was added. Solution was left stirring at room temperature for 5 h. Upon completion, the reaction mixture was diluted with water (100 ml) and the mixture was frozen and lyophilized. The resultant white powder was then purified using flash chromatography (silica, $CHCl_3$:DCM, 1:1, UV). The desired product, Ch-A-Epo1-OMe (0.007 mmol, 3.7 mg, 70% yield) was obtained as a white powder. HRMS (ESI, +ve) $C_{27}H_{36}Cl_2O_6$ $[M+H]^+$ calculated for 527.1962, found 527.1963.

| H | $\delta_H$ | m | J(Hz) | COSY | ROESY | C | $\delta_C$ | HMBC |
|---|---|---|---|---|---|---|---|---|
| — | | | | | — | 1 | 168.0 | |
| 2 | 4.54 | q | 7.0 | 23 | 23 | 2 | 47.2 | 23, 1, 3 |
| — | | | | | | 3 | 192.1 | |
| — | | | | | | 4 | 81.4 | |
| — | | | | | | 5 | 196.7 | |
| 6 | 3.83 | dd | 11.8, 6.8 | 7, 15 | 9, 15, 24, 12 | 6 | 49.6 | 5, 7, 12, 16, 15 |
| 7 | 2.34 | td | 11.1, 3.8 | 6 | 6, 8, 11α, 26, | 7 | 34.4 | 8, 12, 24 |
| 8 | 2.01-2.05 | m | | 9, 7, 24 | 9, 7, 24 | 8 | 37.5 | 8, 12, 24 |
| 9 | 3.60 | bs | | 8, 11β | 6, 8, 24 | 9 | 76.14 | 7, 8, 10, 11, 16, 22, 24 |
| — | | | | | — | 10 | 77.1 | |
| 11α | 1.42 | t | 13.3 | 12, 11β | 7, 11β | 11 | 38.2 | 7, 9 |
| 11β | 1.76 | d | 13.7 | 11α, 9, 12, 7 | 11α, 12, 27 | | | |
| 12 | 2.29-2.29 | m | | 11α, 11β, 8, | 6, 24 | 12 | 28.8 | 11, 14, 13 |
| 13 | 5.59-5.64 | m | | | | 13 | 133.9 | |
| 14 | 5.49-5.52 | m | | | | 14 | 124.0 | |
| 15 | 3.01-3.05 | m | | 16, 6, 12 | 6, 16 | 15 | 43.1 | |
| 16 | 2.74-2.78 | m | | 15, 26, | 15, 26 | 16 | 33.5 | |
| 17 | 5.33 | t | 9.3 | 16, 18 | 18 | 17 | 139.3 | 16, 19, 20, 26, 18 |
| 18 | 5.88 | t | 10.9 | 19, 17 | 17, 21/13, 20/14 | 18 | 125.6 | 16, 19, 20 |
| 19 | 6.05 | t | 13.3 | 18, 20/14 | 16, 15 | 19 | 124.0 | 18, 17, 21 |
| 20 | 5.49-5.52 | m | | | | 20 | 130.4 | |
| 21 | 5.59-5.64 | m | | | | 21 | 70.4 | |
| 22 | 1.33 | d | 6.7 | 21/13 | 21/13, 20/14 | 22 | 22.1 | 20, 21 |
| 23 | 1.65 | d | 7.1 | 2 | 2 | 23 | 17.1 | 3, 1, 2 |
| 24 | 1.02 | d | 7.5 | 8 | 6, 8, 9, 12, 25 | 24 | 12.3 | 8, 7, 9 |
| 25 | 1.22 | s | | | 9, 11α, 24, 27 | 25 | 21.7 | 9, 10, 11 |
| 26 | 0.98 | d | 6.4 | 16 | 7, 16 | 26 | 15.8 | 17, 15, 16 |
| 27 | 3.18 | s | | | 9, 24, 25 | 27 | 48.7 | 10 |

Ch-A-Epo1-OEt:

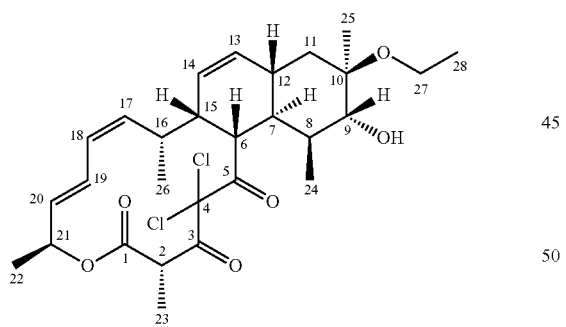

Ch-A-Epo1-OEt

Ch-A-Epo1-OEt (65% yield), white powder was prepared following the same procedure described above for compound Ch-A-Epo1-OMe with the use of ethanol instead of methanol. HRMS (ESI, +ve) $C_{28}H_{38}Cl_2O_6$ [M+H]$^+$ calculated for 541.2118, found 541.2117.

| H | $\delta_H$ | m | J(Hz) | COSY | ROESY | C | $\delta_C$ | HMBC |
|---|---|---|---|---|---|---|---|---|
| — | | | | | — | 1 | 168.0 | |
| 2 | 4.54 | q | 7.0 | 23 | 23 | 2 | 47.2 | 23, 1, 3 |
| — | | | | | | 3 | 192.1 | |
| — | | | | | | 4 | 81.4 | |

| H | $\delta_H$ | m | J(Hz) | COSY | ROESY | C | $\delta_C$ | HMBC |
|---|---|---|---|---|---|---|---|---|
| — | | | | | | 5 | 196.7 | |
| 6 | 3.83 | dd | 11.8, 6.8 | 7, 15 | 9, 15, 24, 12 | 6 | 49.6 | 5, 7, 12, 16, 15 |
| 7 | 2.34 | td | 11.1, 3.8 | 6 | 6, 8, 11α, 26, | 7 | 34.4 | 8, 12, 24 |
| 8 | 2.01-2.05 | m | | 9, 7, 24 | 9, 7, 24 | 8 | 37.5 | 8, 12, 24 |
| 9 | 3.60 | bs | | 8, 11β | 6, 8, 24 | 9 | 76.14 | 7, 8, 10, 11, 16, 22, 24 |
| — | | | | | — | 10 | 77.1 | |
| 11α | 1.42 | t | 13.3 | 12, 11β | 7, 11β | 11 | 38.2 | 7, 9 |
| 11β | 1.76 | d | 13.7 | 11α, 9, 12, 7 | 11α, 12, 27 | | | |
| 12 | 2.29-2.29 | m | | 11α, 11β, 8, | 6, 24 | 12 | 28.8 | 11, 14, 13 |
| 13 | 5.59-5.64 | m | | | | 13 | 133.9 | |
| 14 | 5.49-5.52 | m | | | | 14 | 124.0 | |
| 15 | 3.01-3.05 | m | | 16, 6, 12 | 6, 16 | 15 | 43.1 | |
| 16 | 2.74-2.78 | m | | 15, 26, | 15, 26 | 16 | 33.5 | |
| 17 | 5.33 | t | 9.3 | 16, 18 | 18 | 17 | 139.3 | 16, 19, 20, 26, 18 |
| 18 | 5.88 | t | 10.9 | 19, 17 | 17, 21/13, 20/14 | 18 | 125.6 | 16, 19, 20 |
| 19 | 6.05 | t | 13.3 | 18, 20/14 | 16, 15 | 19 | 124.0 | 18, 17, 21 |
| 20 | 5.49-5.52 | m | | | | 20 | 130.4 | |
| 21 | 5.59-5.64 | m | | | | 21 | 70.4 | |
| 22 | 1.33 | d | 6.7 | 21/13 | 21/13, 20/14 | 22 | 22.1 | 20, 21 |
| 23 | 1.65 | d | 7.1 | 2 | 2 | 23 | 17.1 | 3, 1, 2 |
| 24 | 1.02 | d | 7.5 | 8 | 6, 8, 9, 12, 25 | 24 | 12.3 | 8, 7, 9 |
| 25 | 1.22 | s | | | 9, 11α, 24, 27 | 25 | 21.7 | 9, 10, 11 |
| 26 | 0.98 | d | 6.4 | 16 | 7, 16 | 26 | 15.8 | 17, 15, 16 |
| 27 | 3.36-3-43 | m | | 28 | 9, 24, 25 | 27 | 56.7 | 10, 28 |
| 28 | 1.13 | t | 6.9 | 27 | | 28 | 16.1 | 28 |

Ch-A-Epo1-Cl:

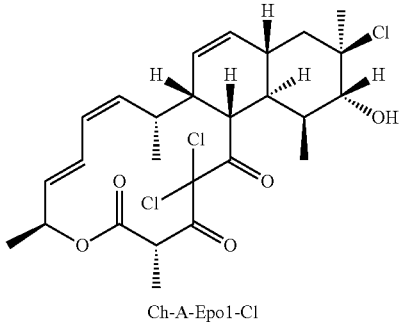

Ch-A-Epo1-Cl

Ch-A-Epo1 (0.01 mmol, 5 mg) was dissolved in CHCl$_3$ (2 ml) and concentrated hydrochloric acid (12 N, 50 μL) was added. Solution was left stirring at room temperature for 5 h. Upon completion, the reaction mixture was diluted with water (100 ml) and the mixture was frozen and lyophilized. The resultant white powder was then purified using flash chromatography (silica, CHCl$_3$:DCM, 1:1, UV). The desired product, Ch-A-Epo1-Cl (88% yield) was obtained as a white powder. HRMS (ESI, +ve) C$_{26}$H$_{33}$Cl$_3$O$_5$ [M+H]$^+$ calculated for 531.1466, found 531.1465.

Ch-A-Epo2-OMe:

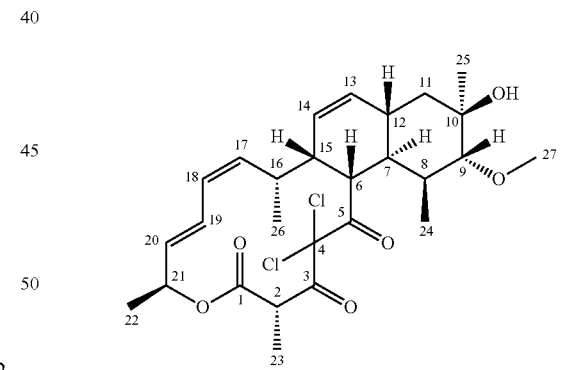

Ch-A-Epo2-OMe

Ch-A-Epo2-OMe (85% yield), white powder was prepared following the same procedure described above for compound Ch-A-Epo1-OMe. HRMS (ESI, +ve) C$_{27}$H$_{36}$Cl$_2$O$_6$ [M+H]$^+$ calculated for 527.1962, found 527.1963.

| H | $\delta_H$ | M | J(Hz) | COSY | ROESY | C | $\delta_C$ | HMBC |
|---|---|---|---|---|---|---|---|---|
| — | | | | | | 1 | 168.0 | |
| 2 | 4.54 | q | 7.0 | 23 | — | 2 | 47.2 | 23, 1, 3 |

| H | $\delta_H$ | M | J(Hz) | COSY | ROESY | C | $\delta_C$ | HMBC |
|---|---|---|---|---|---|---|---|---|
| — | | | | | | 3 | 192.1 | |
| — | | | | | | 4 | 81.3 | |
| — | | | | | | 5 | 196.9 | |
| 6 | 3.81 | dd | 12.0, 6.3 | 7, 12, 15 | 15, 24, 12 | 6 | 49.9 | 5, 8, 12, 16, 15 |
| 7 | 2.23 | td | 11.75, 3.95 | 6, 12, | 24 | 7 | 34.3 | 6, 8, 9, 11, 12, 15, 24, 25, 13 |
| 8 | 2.32-2.34 | m | | 9, 7, 24 | 9, 6 | 8 | 29.6 | 9, 10, 7, 24 |
| 9 | 2.86 | bs | | 8, 11α, 25, 24 | 8, 25, 24 | 9 | 88.4 | 10, 24, 8, 16, 11, 27 |
| — | | | | | | 10 | 73.5 | |
| 11α | 1.56 | ddd | 13.7, 3.5, 1.3 | 9, 12, 11β | 25, 13, 7 | 11 | 42.5 | 9, 10, 7, 8, 13 |
| 11β | 1.47-1.52 | m | | 9, 12, 11α | — | | | |
| 12 | 2.39-2.43 | m | | 7, 11α, 11β, 13, 14 | 6, 24 | 12 | 28.9 | |
| 13 | 5.59-5.66 | m | | 14, 15, 7 | 17, 12, 15, 11α | 13 | 133.9 | |
| 14 | 5.46-5.54 | m | | 13, 15, 16 | 17, 15 | 14 | 123.9 | |
| 15 | 3.01-3.05 | m | | 16, 6, 12, 13, 14 | 6, 16, 19, 14, 13 | 15 | 43.2 | |
| 16 | 2.71-2.79 | m | | 15, 26, 17, 18 | 15, 19, 18, 17, 14 | 16 | 33.6 | 15, 19, 17, 26, 14 |
| 17 | 5.33 | t | 9.3 | 16, 18, 19 | 26, 14, 13 | 17 | 139.3 | 26, 16, 18, 19, 20, 15 |
| 18 | 5.88 | t | 11 | 19, 17 | 20 | 18 | 125.7 | 16, 15, 19, 20 |
| 19 | 6.01-6.09 | m | | 18, 20, 17 | 16, 15, 17, 21 | 19 | 124.0 | 21, 18, 20, 17 |
| 20 | 5.46-5.54 | m | | 19, 21 | 22 | 20 | 130.3 | |
| 21 | 5.59-5.66 | m | | 22, 20 | — | 21 | 70.4 | |
| 22 | 1.32 | d | 6.7 | 21 | 20 | 22 | 22.1 | 20, 21, 23 |
| 23 | 1.65 | d | 7.0 | 2 | — | 23 | 17.1 | 3, 1, 2 |
| 24 | 1.03 | d | 7.6 | 8, 9, 7 | 6, 9, 12 | 24 | 12.4 | 8, 7, 9, 12 |
| 25 | 1.27 | s | | | 9, 11 | 25 | 29.3 | 9, 10, 11 |
| 26 | 0.97 | d | 6.4 | 16 | 7 | 26 | 15.7 | 17, 15, 16, 18 |
| 27 | 3.39 | s | | | 8, 9 | 27 | 57.3 | 9 |
Ch-A-Epo2-OEt:
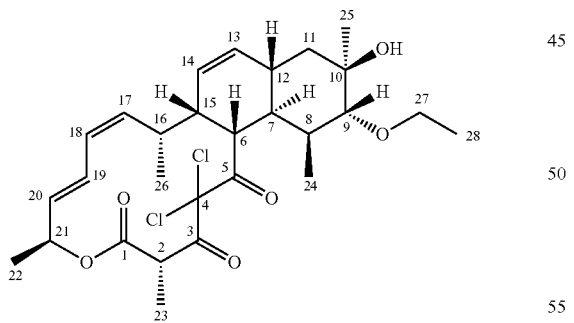
Ch-A-Epo2-OEt
Ch-A-Epo2-OEt (82% yield), white powder was prepared following the same procedure described above for compound Ch-A-Epo1-OEt. HRMS (ESI, +ve) $C_{28}H_{38}Cl_2O_6$ [M+H]$^+$ calculated for 541.2118, found 541.2117.
| H | $\delta_H$ | M | J(Hz) | COSY | ROESY | C | $\delta_C$ | HMBC |
|---|---|---|---|---|---|---|---|---|
| — | | | | | — | 1 | 168.0 | |
| 2 | 4.54 | q | 7.0 | 23 | — | 2 | 47.2 | 23, 1, 3 |

| H | $\delta_H$ | M | J(Hz) | COSY | ROESY | C | $\delta_C$ | HMBC |
|---|---|---|---|---|---|---|---|---|
| — | | | | | | 3 | 192.1 | |
| — | | | | | | 4 | 81.3 | |
| — | | | | | | 5 | 196.9 | |
| 6 | 3.81 | dd | 12.0, 6.3 | 7, 12, 15 | 15, 24, 12 | 6 | 49.9 | 5, 8, 12, 16, 15 |
| 7 | 2.23 | td | 11.7, 3.9 | 6, 12, | 24 | 7 | 34.3 | 6, 8, 9, 11, 12, 15, 24, 25, 13 |
| 8 | 2.32-2.34 | m | | 9, 7, 24 | 9, 6 | 8 | 29.6 | 9, 10, 7, 24 |
| 9 | 2.86 | bs | | 8, 11α, 25, 24 | 8, 25, 24 | 9 | 88.4 | 10, 24, 8, 16, 11, 27 |
| — | | | | | | 10 | 73.5 | |
| 11α | 1.56 | ddd | 13.7, 3.5, 1.3 | 9, 12, 11β | 25, 13, 7 | 11 | 42.5 | 9, 10, 7, 8, 13 |
| 11β | 1.47-1.52 | m | | 9, 12, 11α | — | | | |
| 12 | 2.39-2.43 | m | | 7, 11α, 11β, 13, 14 | 6, 24 | 12 | 28.9 | |
| 13 | 5.59-5.66 | m | | 14, 15, 7 | 17, 12, 15, 11α | 13 | 133.9 | |
| 14 | 5.46-5.54 | m | | 13, 15, 16 | 17, 15 | 14 | 123.9 | |
| 15 | 3.01-3.05 | m | | 16, 6, 12, 13, 14 | 6, 16, 19, 14, 13 | 15 | 43.2 | |
| 16 | 2.71-2.79 | m | | 15, 26, 17, 18 | 15, 19, 18, 17, 14 | 16 | 33.6 | 15, 19, 17, 26, 14 |
| 17 | 5.33 | t | 9.3 | 16, 18, 19 | 26, 14, 13 | 17 | 139.3 | 26, 16, 18, 19, 20, 15 |
| 18 | 5.88 | t | 11 | 19, 17 | 20 | 18 | 125.7 | 16, 15, 19, 20 |
| 19 | 6.01-6.09 | m | | 18, 20, 17 | 16, 15, 17, 21 | 19 | 124.0 | 21, 18, 20, 17 |
| 20 | 5.46-5.54 | m | | 19, 21 | 22 | 20 | 130.3 | |
| 21 | 5.59-5.66 | m | | 22, 20 | — | 21 | 70.4 | |
| 22 | 1.32 | d | 6.7 | 21 | 20 | 22 | 22.1 | 20, 21, 23 |
| 23 | 1.65 | d | 7.0 | 2 | — | 23 | 17.1 | 3, 1, 2 |
| 24 | 1.03 | d | 7.6 | 8, 9, 7 | 6, 9, 12 | 24 | 12.4 | 8, 7, 9, 12 |
| 25 | 1.27 | s | | | 9, 11 | 25 | 29.3 | 9, 10, 11 |
| 26 | 0.97 | d | 6.4 | 16 | 7 | 26 | 15.7 | 17, 15, 16, 18 |
| 27α | 3.34-3.38 | m | | 28, 27α | 8, 9 | 27 | 64.9 | 9 |
| 27β | 3.70-3.75 | m | | 28, 27β | | | | |
| 28 | 1.92 | t | 7.0 | 27 | | 28 | 15.7 | |

Ch-A-Epo2-OBu:

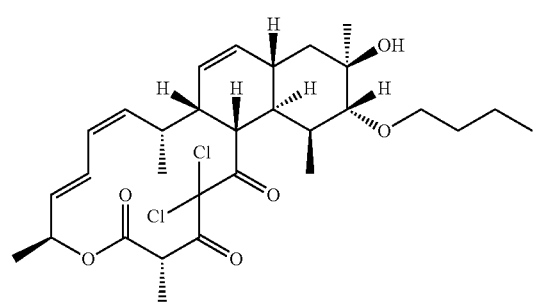

Ch-A-Epo2-OBu

Ch-A-Epo2-OBu (90% yield), white powder was prepared following the same procedure described above for compound Ch-A-Epo1-OMe where 1-butanol was used instead of methanol. HRMS (ESI, +ve) $C_{30}H_{42}Cl_2O_6$ [M+H]$^+$ calculated for 569.2431, found 569.2433.

Ch-A-Epo2-Oisoamyl:

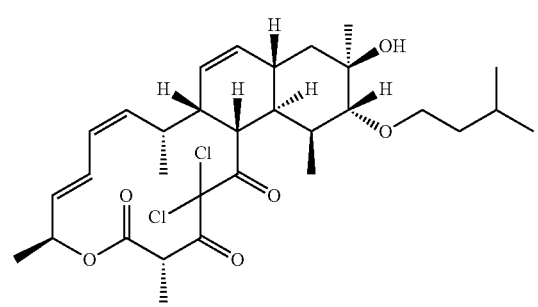

Ch-A-Epo2-Oisoamyl

Ch-A-Epo2-Oisoamyl (80% yield), white powder was prepared following the same procedure described above for compound Ch-A-Epo1-OMe where isomayl alcohol was used instead of methanol. HRMS (ESI, +ve) $C_{31}H_{44}Cl_2O_6$ [M+H]$^+$ calculated for 583.2588, found 583.2587.

Ch-A-Epo2-OBuOH:

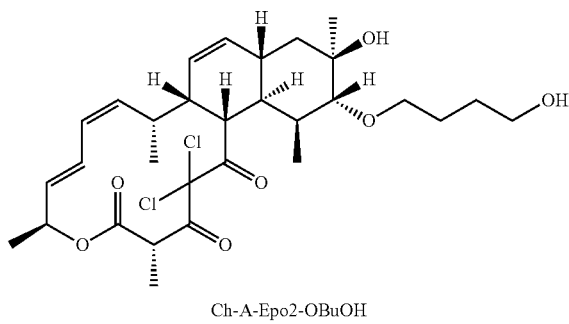

Ch-A-Epo2-OBuOH

Ch-A-Epo2-OBuOH (65% yield), white powder was prepared following the same procedure described above for compound Ch-A-Epo1-OMe where 1,4-butanediol:THF (1:1) was used instead of methanol. HRMS (ESI, +ve) $C_{30}H_{42}Cl_2O_7$ [M+H]$^+$ calculated for 585.2380, found 585.2381.

Ch-A-Epo2-Cl:

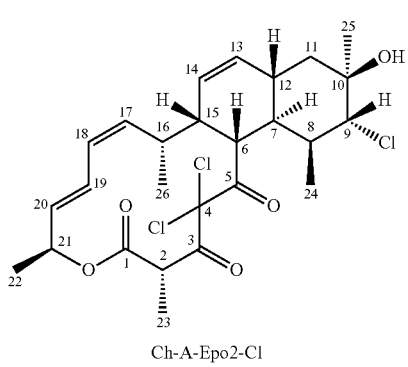

Ch-A-Epo2-Cl

Ch-A-Epo2-Cl (95% yield), white powder was prepared following the same procedure described above for compound Ch-A-Epo1-Cl. HRMS (ESI, +ve) $C_{26}H_{33}Cl_3O_5$ [M+H]$^+$ calculated for 531.1466, found 531.1465.

| H | $\delta_H$ | M | J(Hz) | COSY | ROESY | C | $\delta_C$ | HMBC |
|---|---|---|---|---|---|---|---|---|
| — | | | | | | 1 | 168.0 | — |
| 2 | 4.53 | q | 7.0 | 23 | — | 2 | 47.3 | 23, 1, 3 |
| — | | | | | | 3 | 192.1 | |
| — | | | | | | 4 | 81.3 | |
| — | | | | | | 5 | 196.9 | |
| 6 | 3.81 | dd | 11.7, 6.7 | 7, 12, 15 | 15, 24, 12 | 6 | 49.8 | 5, 8, 12, 16, 15 |
| 7 | 2.57 | td | 11.3, 3.8 | 6, 12, | 24 | 7 | 33.9 | 6, 8, 9, 11, 12, 15, 24, 25, 13 |
| 8 | 2.43-2.49 | m | | 9, 7, 24 | 9, 6 | 8 | 29.6 | 9, 10, 7, 24 |
| 9 | 3.84 | t | 1.7 | 8, 11α, 25, 24 | 8, 25, 24 | 9 | 70.1 | 10, 24, 8, 16, 11, 27 |
| — | | | | | | 10 | 73.5 | |
| 11α | 1.68-1.73 | m | | 9, 12, 11β | 25, 13, 7 | 11 | 41.0 | 9, 10, 7, 8, 13 |
| 11β | 1.68-1.73 | m | | 9, 12, 11α | — | | | |
| 12 | 2.43-2.49 | m | | 7, 11α, 11β, 13, 14 | 6, 24 | 12 | 28.6 | |
| 13 | 5.60-5.65 | m | | 14, 15, 7 | 17, 12, 15, 11α | 13 | 133.4 | |
| 14 | 5.50-5.54 | m | | 13, 15, 16 | 17, 15 | 14 | 124.5 | |
| 15 | 3.01-3.08 | m | | 16, 6, 12, 13, 14 | 6, 16, 19, 14, 13 | 15 | 43.3 | |
| 16 | 2.74-2.82 | m | | 15, 26, 17, 18 | 15, 19, 18, 17, 14 | 16 | 33.6 | 15, 19, 17, 26, 14 |
| 17 | 5.33 | t | 9.3 | 16, 18, 19 | 26, 14, 13 | 17 | 139.3 | 26, 16, 18, 19, 20, 15 |
| 18 | 5.89 | t | 10.9 | 19, 17 | 20 | 18 | 125.7 | 16, 15, 19, 20 |
| 19 | 6.06 | t | 12.9 | 18, 20, 17 | 16, 15, 17, 21 | 19 | 124.0 | 21, 18, 20, 17 |
| 20 | 5.50-5.54 | m | | 19, 21 | 22 | 20 | 130.4 | |
| 21 | 5.60-5.65 | m | | 22, 20 | — | 21 | 70.3 | |
| 22 | 1.33 | d | 6.7 | 21 | 20 | 22 | 21.2 | 20, 21, 23 |
| 23 | 1.65 | d | 7.0 | 2 | — | 23 | 17.2 | 3, 1, 2 |
| 24 | 1.13 | d | 7.7 | 8, 9, 7 | 6, 9, 12 | 24 | 14.8 | 8, 7, 9, 12 |
| 25 | 1.40 | s | | | 9, 11 | 25 | 31.1 | 9, 10, 11 |
| 26 | 1.01 | d | 6.5 | 16 | 7 | 26 | 15.8 | 17, 15, 16, 18 |

Ch-A-Epo2-Br:

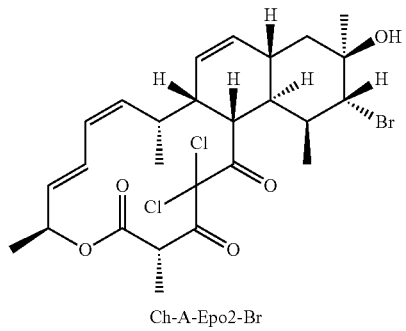

Ch-A-Epo2-Br

Ch-A-Epo2-Br (70% yield), white powder was prepared following the same procedure described above for compound Ch-A-Epo1-Cl where HBr (purum ≥62%) was used instead of HCl and THF as a solvent instead of $CHCl_3$. HRMS (ESI, +ve) $C_{26}H_{33}BrCl_2O_5$ [M+H]$^+$ calculated for 575.0961, found 575.0962.

Ch-A-Epo2-OH:

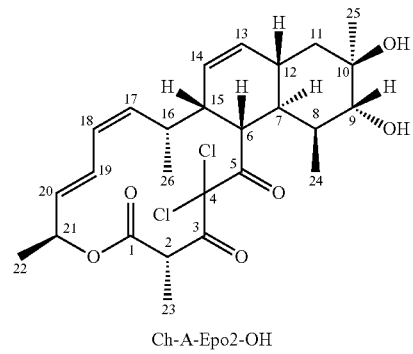

Ch-A-Epo2-OH

Ch-A-Epo2-OH (50% yield), white powder was prepared following the same procedure described above for compound Ch-A-Epo1-OMe where a mixture of THF:water (1:1) was used as a solvent instead of methanol. HRMS (ESI, +ve) $C_{26}H_{34}Cl_2O_6$ [M+H]$^+$ calculated for 513.1805, found 513.1805.

| H | $\delta_H$ | M | J(Hz) | COSY | ROESY | C | $\delta_C$ | HMBC |
|---|---|---|---|---|---|---|---|---|
| — | | | | | — | 1 | 168.0 | |
| 2 | 4.55 | q | 7.0 | 23 | — | 2 | 47.5 | 23, 1, 3 |
| — | | | | | | 3 | 192.1 | |
| — | | | | | | 4 | 81.3 | |
| — | | | | | | 5 | 196.9 | |
| 6 | 3.84 | dd | 11.8, 6.8 | 7, 12, 15 | 15, 24, 12 | 6 | 49.7 | 5, 8, 12, 16, 15 |
| 7 | 2.35 | td | 11.3, 3.9 | 6, 12, | 24 | 7 | 34.6 | 6, 8, 9, 11, 12, 15, 24, 25, 13 |
| 8 | 2.41-2.47 | m | | 9, 7, 24 | 9, 6 | 8 | 37.5 | 9, 10, 7, 24 |
| 9 | 3.47 | d | 2.0 | 8, 11α, 25, 24 | 8, 25, 24 | 9 | 79.1 | 10, 24, 8, 16, 11, 27 |
| — | | | | | — | 10 | 73.5 | |
| 11α | 1.58-1.60 | m | | 9, 12, 11β | 25, 13, 7 | 11 | 42.1 | 9, 10, 7, 8, 13 |
| 11β | 1.58-1.60 | m | | 9, 12, 11α | — | | | |
| 12 | 2.41-2.47 | m | | 7, 11α, 11β, 13, 14 | 6, 24 | 12 | 29.5 | |
| 13 | 5.59-5.65 | m | | 14, 15, 7 | 17, 12, 15, 11α | 13 | 132.9 | |
| 14 | 5.48-5.54 | m | | 13, 15, 16 | 17, 15 | 14 | 124.2 | |
| 15 | 3.01-3.06 | m | | 16, 6, 12, 13, 14 | 6, 16, 19, 14, 13 | 15 | 43.4 | |
| 16 | 2.73-2.79 | m | | 15, 26, 17, 18 | 15, 19, 18, 17, 14 | 16 | 33.7 | 15, 19, 17, 26, 14 |
| 17 | 5.33 | t | 9.3 | 16, 18, 19 | 26, 14, 13 | 17 | 139.4 | 26, 16, 18, 19, 20, 15 |
| 18 | 5.89 | t | 10.9 | 19, 17 | 20 | 18 | 125.8 | 16, 15, 19, 20 |
| 19 | 6.03-6.08 | m | | 18, 20, 17 | 16, 15, 17, 21 | 19 | 124.2 | 21, 18, 20, 17 |
| 20 | 5.48-5.54 | m | | 19, 21 | 22 | 20 | 130.7 | |
| 21 | 5.59-5.65 | m | | 22, 20 | — | 21 | 70.9 | |
| 22 | 1.33 | d | 6.6 | 21 | 20 | 22 | 22.1 | 20, 21, 23 |
| 23 | 1.66 | d | 7.0 | 2 | — | 23 | 17.1 | 3, 1, 2 |
| 24 | 1.07 | d | 7.6 | 8, 9, 7 | 6, 9, 12 | 24 | 12.1 | 8, 7, 9, 12 |
| 25 | 1.31 | m | | | 9, 11 | 25 | 28.7 | 9, 10, 11 |
| 26 | 0.98 | d | 6.5 | 16 | 7 | 26 | 15.7 | 17, 15, 16, 18 |

Ch-A-Epo2-ONO₂:

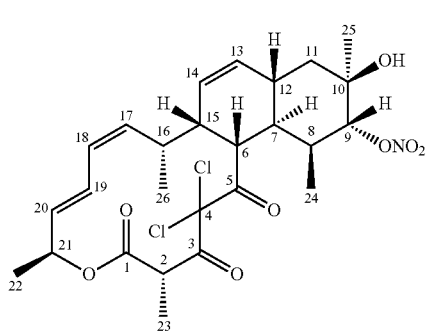

Ch-A-Epo2-ONO₂

Ch-A-Epo2-F:

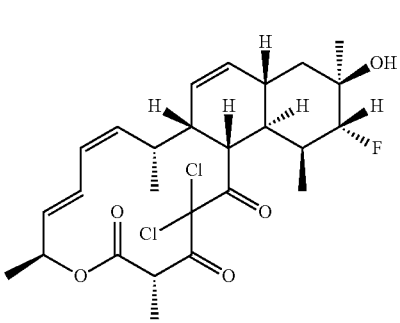

Ch-A-Epo2-F

Ch-A-Epo2-ONO₂ (80% yield), white powder was prepared following the same procedure described above for compound Ch-A-Epo1-Cl where HNO₃ 69% was used instead of HCl and THF as a solvent. HRMS (ESI, +ve) $C_{26}H_{33}Cl_2NO_8$ [M+H]⁺ calculated for 558.1656, found 558.1654.

Ch-A-Epo2-F (40% yield), white powder was prepared following the same procedure described above for compound Ch-A-Epo1-Cl where HF (48 wt. % in H₂O) was used instead of HCl and THF as a solvent and the reaction was done in a flacon tube. HRMS (ESI, +ve) $C_{26}H_{33}Cl_2FO_5$ [M+H]⁺ calculated for 515.1762, found 515.1761.

| H | $\delta_H$ | M | J(Hz) | COSY | ROESY | C | $\delta_C$ | HMBC |
|---|---|---|---|---|---|---|---|---|
| — | | | | | — | 1 | 168.0 | |
| 2 | 4.52 | q | 7.0 | 23 | — | 2 | 47.6 | 23, 1, 3 |
| — | | | | | | 3 | 192.1 | |
| — | | | | | | 4 | 81.3 | |
| — | | | | | | 5 | 196.9 | |
| 6 | 3.79 | dd | 11.8, 6.8 | 7, 12, 15 | 15, 24, 12 | 6 | 50.0 | 5, 8, 12, 16, 15 |
| 7 | 2.20 | td | 11.3, 4.1 | 6, 12, | 24 | 7 | 35.1 | 6, 8, 9, 11, 12, 15, 24, 25, 13 |
| 8 | 2.29-2.34 | m | | 9, 7, 24 | 9, 6 | 8 | 32.6 | 9, 10, 7, 24 |
| 9 | 4.81 | t | 1.7 | 8, 11α, 25, 24 | 8, 25, 24 | 9 | 88.2 | 10, 24, 8, 16, 11, 27 |
| — | | | | | — | 10 | 73.5 | |
| 11α | 1.71-1.73 | m | | 9, 12, 11β | 25, 13, 7 | 11 | 43.2 | 9, 10, 7, 8, 13 |
| 11β | 1.47 | t | 13.4 | 9, 12, 11α | — | | | |
| 12 | 2.44-2.48 | m | | 7, 11α, 11β, 13, 14 | 6, 24 | 12 | 28.6 | |
| 13 | 5.58-5.63 | m | | 14, 15, 7 | 17, 12, 15, 11α | 13 | 132.9 | |
| 14 | 5.50-5.54 | m | | 13, 15, 16 | 17, 15 | 14 | 123.9 | |
| 15 | 3.03-3.06 | m | | 16, 6, 12, 13, 14 | 6, 16, 19, 14, 13 | 15 | 43.2 | |
| 16 | 2.73-2.77 | m | | 15, 26, 17, 18 | 15, 19, 18, 17, 14 | 16 | 33.6 | 15, 19, 17, 26, 14 |
| 17 | 5.30-5.33 | m | | 16, 18, 19 | 26, 14, 13 | 17 | 139.2 | 26, 16, 18, 19, 20, 15 |
| 18 | 5.88 | t | 10.8 | 19, 17 | 20 | 18 | 125.8 | 16, 15, 19, 20 |
| 19 | 6.02-6.07 | m | | 18, 20, 17 | 16, 15, 17, 21 | 19 | 124.0 | 21, 18, 20, 17 |
| 20 | 5.50-5.54 | m | | 19, 21 | 22 | 20 | 130.7 | |
| 21 | 5.58-5.63 | m | | 22, 20 | — | 21 | 70.6 | |
| 22 | 1.32-1.35 | m | | 21 | 20 | 22 | 21.1 | 20, 21, 23 |
| 23 | 1.64 | d | 7.0 | 2 | — | 23 | 17.1 | 3, 1, 2 |
| 24 | 1.13 | d | 7.6 | 8, 9, 7 | 6, 9, 12 | 24 | 12.1 | 8, 7, 9, 12 |
| 25 | 1.32-1.35 | m | | | 9, 11 | 25 | 28.7 | 9, 10, 11 |
| 26 | 0.96 | d | 6.5 | 16 | 7 | 26 | 15.7 | 17, 15, 16, 18 |

Ch-A-Epo2-Glycerol:

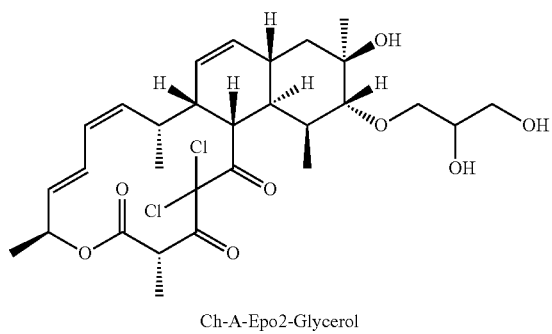

Ch-A-Epo2-Glycerol

Ch-A-Epo2-Glycerol (45% yield), white powder was prepared following the same procedure described above for compound Ch-A-Epo1-OMe where glycerol:THF (1:1) was used instead of methanol. HRMS (ESI, +ve) $C_{29}H_{40}Cl_2O_8$ $[M+H]^+$ calculated for 587.2173, found 587.2175.

Ch-A-Epo2-OBn:

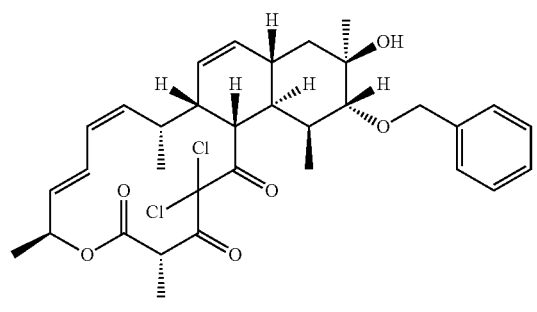

Ch-A-Epo2-OBn

Ch-A-Epo2-OBn (50% yield), white powder was prepared following the same procedure described above for compound Ch-A-Epo1-OMe where benzyl alcohol:THF (1:1) was used instead of methanol. HRMS (ESI, +ve) $C_{33}H_{40}Cl_2O_6$ $[M+H]^+$ calculated for 603.2275, found 603.2272.

Ch-B-Epo-Cl:

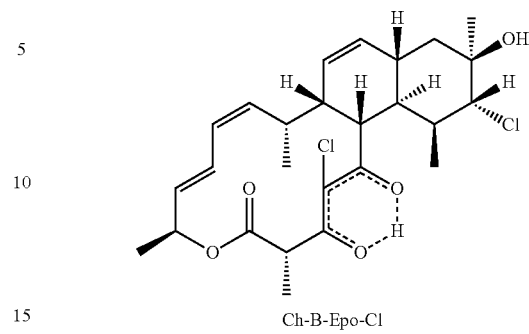

Ch-B-Epo-Cl

Ch-B-Epo-Cl (80% yield), white powder was prepared from Ch-B-Epo following the same procedure described above for compound Ch-A-Epo1-Cl. HRMS (ESI, +ve) $C_{26}H_{34}Cl_2O_5$ $[M+H]^+$ calculated for 497.1856, found 497.1856.

Ch-B1-Epo-OMe:

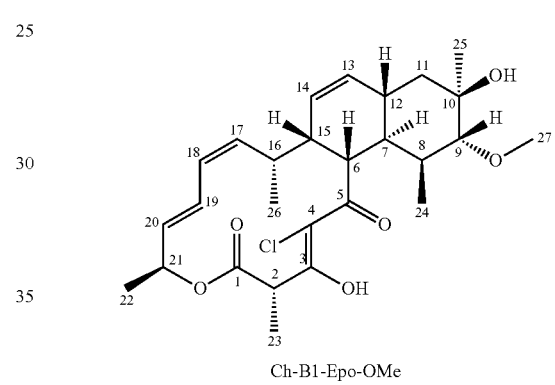

Ch-B1-Epo-OMe

Ch-B1-Epo-OMe (53% yield), white powder was prepared from Ch-B1-Epo following the same procedure described above for compound Ch-A-Epo1-OMe. Extraction of the reaction with dichloromethane was accomplished before purification instead of freeze drying. HRMS (ESI, +ve) $C_{27}H_{37}ClO_6$ $[M+H]^+$ calculated for 493.2351, found 493.2346.

| H | $\delta_H$ | m | J(Hz) | COSY | C | $\delta_C$ | HMBC |
|---|---|---|---|---|---|---|---|
| — | | | | | 1 | 168.0 | — |
| 2 | 4.40 | q | 6.9 | 23 | 2 | 44.9 | 23, 1, 3 |
| — | | | | | 3 | 188.6 | — |
| — | | | | | 4 | 109.4 | — |
| — | | | | | 5 | 193.4 | — |
| 6 | 3.50 | dd | 12.3, 6.7 | 7, 15 | 6 | 46.7 | 5, 4, 15, 7, 12 |
| 7 | 2.21 | td | 17.5, 4.3 | 6, 8, 12 | 7 | 33.3 | 24, 8, 12, 11/15, 6 |
| 8 | 2.45-2.49 | m | | 7, 24 | 8 | 30.7 | 24, 7, 12, 9, 10 |
| 9 | 2.83 | br s | | 8 | 9 | 88.4 | 24, 25, 7, 11, 27, 10 |
| — | — | | | | 10 | 73.6 | — |
| 11α | 1.51 | q | 13.0 | 12 | 11 | 42.2 | 12, 7, 10, 9, 13 |
| 11β | 1.54 | m | | 12 | | | 12, 7, 10, 9, 13 |
| 12 | 2.40-2.45 | m | | 7, 11 | 12 | 29.4 | |
| 13 | 5.62 | d | 10.0 | 14, 15, 12 | 13 | 133.9 | 11, 12, 7, 14 |

-continued
| H | $\delta_H$ | m | J(Hz) | COSY | C | $\delta_C$ | HMBC |
|---|---|---|---|---|---|---|---|
| 14 | 5.50 | ddd | 10.1, 4.2, 2.7 | 13, 15, 12 | 14 | 124.7 | 13, 12, 15, 6 |
| 15 | 2.76-2.80 | m | | 14, 6 | 15 | 42.7 | 7, 14, 13 |
| 16 | 2.56-2.62 | m | | 17, 26, 15 | 16 | 33.2 | 15, 26, 6, 17, 14, 18 |
| 17 | 5.41 | t | 9.6 | 16, 18 | 17 | 139.0 | 16, 19, 26 |
| 18 | 5.88 | t | 10.8 | 19, 17 | 18 | 125.8 | 16, 15, 19, 20 |
| 19 | 6.36 | t | 13.3 | 18, 20 | 19 | 123.4 | 17, 18, 20, 21 |
| 20 | 5.55 | dd | 15.3, 2.2 | 21, 19 | 20 | 131.5 | 22, 21, 18, 19 |
| 21 | 5.45-5.49 | m | | 22, 20 | 21 | 70.4 | 22, 19, 20, 1 |
| 22 | 1.35 | d | 6.6 | 21 | 22 | 20.7 | 20, 21 |
| 23 | 1.44 | d | 7.1 | 2 | 23 | 12.2 | 3, 1, 2 |
| 24 | 0.97 | d | 7.4 | 8 | 24 | 13.0 | 9, 8 |
| 25 | 1.27 | s | | | 25 | 29.2 | 9, 10, 11 |
| 26 | 0.98 | d | 6.2 | 16 | 26 | 16.9 | 16, 15, 17 |
| 27 | 3.36 | s | | | 27 | 57.5 | 9 |
Ch-B1-Epo-OEt:
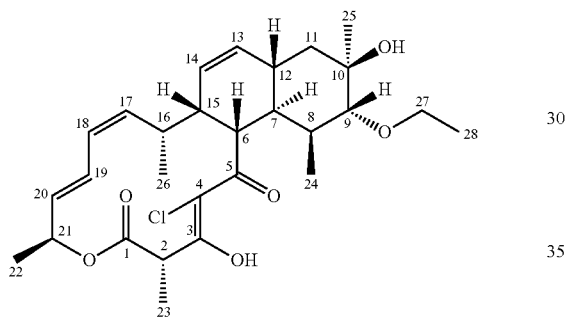
Ch-B1-Epo-OEt
Ch-B1-Epo-OEt (53% yield), white powder was prepared from Ch-B1-Epo following the same procedure described above for compound Ch-B1-Epo-OMe. HRMS (ESI, +ve) $C_{28}H_{39}ClO_6$ [M+H]$^+$ calculated for 507.2508, found 507.2501.
| H | $\delta_H$ | m | J(Hz) | COSY | C | $\delta_C$ | HMBC |
|---|---|---|---|---|---|---|---|
| — | — | | | | 1 | 168.1 | — |
| 2 | 4.40 | q | 6.9 | 23 | 2 | 45.0 | 23, 1, 3, 4 |
| — | — | | | | 3 | 188.8 | — |
| — | — | | | | 4 | 109.3 | — |
| — | — | | | | 5 | 193.0 | — |
| 6 | 3.49 | dd | 12.3, 6.6 | 7, 15 | 6 | 46.8 | 5, 4, 15, 7, 12 |
| 7 | 2.29 | dd | 17.4, 3.9 | 6, 8 | 7 | 33.5 | 24, 8, 12, 11/15, 6 |
| 8 | 2.36-2.47 | m | | 7, 24 | 8 | 31.7 | 24, 7, 9, 10, 12 |
| 9 | 2.92 | br s | | 8 | 9 | 86.5 | 24, 25, 7, 11, 27, 10 |
| — | — | | | | 10 | 73.4 | — |
| 11 | 1.52-1.56 | m | 13.0 | 12 | 11 | 42.3 | 12, 7, 10, 9, 13 |
| 12 | 2.36-2.47 | m | | 7, 11 | 12 | 29.6 | |
| 13 | 5.63 | d | 10.0 | 14, 15, 12 | 13 | 134.1 | 11, 12, 7, 14 |
| 14 | 5.52-5.48 | m | | 13, 15, 12 | 14 | 124.7 | 13, 12, 15, 6 |
| 15 | 2.77 | br s | | 14, 6 | 15 | 43.0 | 7 |

-continued
| H | $\delta_H$ | m | J(Hz) | COSY | C | $\delta_C$ | HMBC |
|---|---|---|---|---|---|---|---|
| 16 | 2.56-2.64 | m | | 17, 26, 15 | 16 | 33.3 | 15, 26, 6, 17, 14, 18 |
| 17 | 5.42 | t | 9.6 | 16, 18 | 17 | 139.3 | 16, 19, 26 |
| 18 | 5.88 | t | 10.8 | 19, 17 | 18 | 126.0 | 16, 15, 19, 20 |
| 19 | 6.36 | t | 16.1 | 18, 20 | 19 | 123.6 | 17, 18, 20, 21 |
| 20 | 5.55 | d | 15.3 | 21, 19 | 20 | 131.6 | 22, 21, 18, 19 |
| 21 | 5.45-5.48 | m | | 22, 20 | 21 | 70.5 | 22, 19, 20, 1 |
| 22 | 1.35 | d | 6.5 | 21 | 22 | 20.9 | 20, 21 |
| 23 | 1.44 | d | 6.9 | 2 | 23 | 12.3 | 3, 1, 2 |
| 24 | 0.95 | d | 7.7 | 8 | 24 | 13.0 | 9, 8, 7 |
| 25 | 1.26 | s | | | 25 | 29.3 | 9, 10, 11 |
| 26 | 0.97 | d | 6.5 | 16 | 26 | 16.8 | 16, 15, 17 |
| 27α | 3.65 | m | | 28, 27β | 27α | 65.1 | 28 |
| 27β | 3.36 | m | | 28, 27α | 27β | | 28 |
| 28 | 1.18 | t | 7.0 | 27α, 27β | 28 | 16.0 | 27 |
Ch-B1-Epo-Cl:
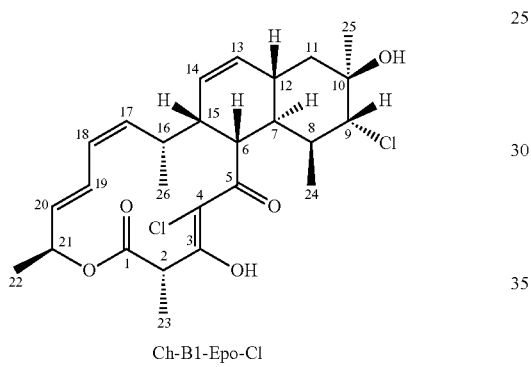
Ch-B1-Epo-Cl
Ch-B1-Epo-Cl (75% yield), white powder was prepared following the same procedure described above for compound Ch-A-Epo1-Cl. HRMS (ESI, +ve) $C_{26}H_{34}Cl_2O_5$ [M+H]$^+$ calculated for 497.1856, found 497.1860.
| H | $\delta_H$ | m | J(Hz) | COSY | C | $\delta_C$ | HMBC |
|---|---|---|---|---|---|---|---|
| — | — | | | | 1 | 168.2 | — |
| 2 | 4.37 | q | 6.9 | 23 | 2 | 44.8 | 23, 1, 3 |
| — | — | | | | 3 | 188.3 | — |
| — | — | | | | 4 | 109.3 | — |
| — | — | | | | 5 | 193.0 | |
| 6 | 3.50 | dd | 11.8, 6.6 | 7, 15 | 6 | 46.5 | 5, 4, 15, 7 |
| 7 | 2.54 | dd | 11.7, 4.0 | 6, 12 | 7 | 32.8 | 6 |
| 8 | 2.56-2.64 | m | | 24 | 8 | 38.2 | |
| 9 | 3.83 | s | 5.4 | | 9 | 70.1 | 10, 7, 11, 24 |
| — | — | | | | 10 | 73.9 | — |
| 11α | 1.72 | t | 13.2 | 12/11β | 11 | 40.7 | 12 |
| 11β | 1.61 | ddd | 13.6, 3.0, 1.7 | 11α | | | 7, 10 |
| 12 | 2.45-2.52 | m | | 11α | 12 | 29.6 | 13 |
| 13 | 5.64 | d | 10.0 | 14 | 13 | 133.3 | 15, 7, 12 |
| 14 | 5.53-5.58 | m | | 13, 15 | 14 | 125.1 | 12, 15 |
| 15 | 2.77-2.84 | m | | 14, 6 | 15 | 42.7 | 16 |
| 16 | 2.57-2.64 | m | | 17, 26 | 16 | 33.1 | |
| 17 | 5.42 | t | 9.6 | 16, 18 | 17 | 138.8 | 16, 19, 20 |
| 18 | 5.89 | t | 10.8 | 19, 17 | 18 | 125.9 | 16, 19, 20 |
| 19 | 6.36 | t | 13.0 | 18, 20 | 19 | 123.4 | 18, 21, 17 |
| 20 | 5.53-5.58 | m | 15.2, 2.1 | 21, 19 | 20 | 131.6 | 21, 18 |
| 21 | 5.45-5.50 | m | | 22 | 21 | 70.5 | 22, 19 |
| 22 | 1.35 | d | 6.7 | 21 | 22 | 20.8 | 20, 21 |
| 23 | 1.43 | d | 7.0 | 2 | 23 | 12.1 | 3, 1, 2 |

| H | $\delta_H$ | m | J(Hz) | COSY | C | $\delta_C$ | HMBC |
|---|---|---|---|---|---|---|---|
| 24 | 1.06 | d | 7.6 | 8 | 24 | 15.3 | 9, 8, 7 |
| 25 | 1.40 | s | | | 25 | 31.1 | 9, 10, 11 |
| 26 | 1.01 | d | 6.5 | 16 | 26 | 16.7 | 16, 15, 17 |

Ch-B1-Epo-ONO$_2$:

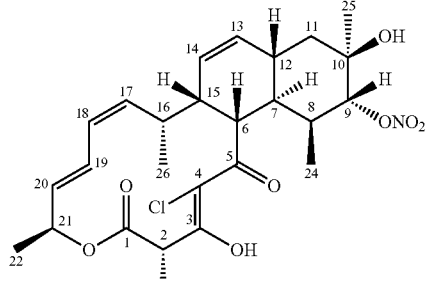

Ch-B1-Epo-ONO$_2$

Ch-A-Epo2-polyEpo:

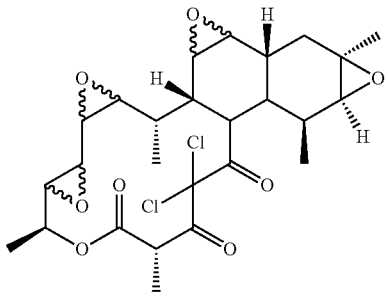

ChA-tetraEpo-A

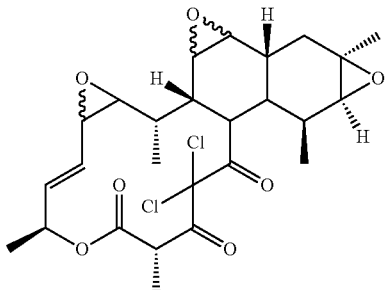

ChA-triEpoA

Ch-B1-Epo-ONO$_2$ (71% yield), white powder was prepared following the same procedure described above for compound Ch-A-Epo1-Cl where HNO$_3$ 69% was used instead of HCl and THF as a solvent. HRMS (ESI, +ve) C$_{26}$H$_{34}$ClNO$_8$ [M+H]$^+$ calculated for 524.2046, found 524.2051.

| H | $\delta_H$ | m | J(Hz) | COSY | C | $\delta_C$ | HMBC |
|---|---|---|---|---|---|---|---|
| — | | | | | 1 | 167.9 | — |
| 2 | 4.37 | q | 7.0 | 23 | 2 | 45.0 | 23, 1, 3, 4 |
| — | | | | | 3 | 188.4 | — |
| — | | | | | 4 | 109.3 | — |
| — | | | | | 5 | 192.2 | — |
| 6 | 3.49 | dd | 12.1, 6.7 | 7, 15 | 6 | 46.4 | 5, 4, 15, 8/16 |
| 7 | 2.18 | td | 17.2, 4.3 | 6, 8 | 7 | 34.4 | 24, 11/15 |
| 8 | 2.3-2.48 | m | | 7, 24 | 8 | 33.2 | 24, 9, 10, 12 |
| 9 | 4.79 | m | | 8, 11α | 9 | 88.3 | 7, 11, 10 |
| — | | | | | 10 | 71.7 | — |
| 11α | 1.71 | ddd | 13.8, 3.0, 1.5 | 11β, 12 | 11 | 42.8 | 7, 10, 9 |
| 11β | 1.46 | t | 13.5 | 11α, 12 | | | 12 |
| 12 | 2.48 | m | | 7, 11, 13 | 12 | 29.3 | |
| 13 | 5.63 | dt | 10.1, 1.5 | 14, 15, 12 | 13 | 133.0 | 11, 12 |
| 14 | 5.55-5.58 | m | | 13, 15, 12 | 14 | 125.5 | 12, 15 |
| 15 | 2.77-2.84 | m | | 14, 6 | 15 | 42.7 | |
| 16 | 2.55-2.62 | m | | 17, 26, 15 | 16 | 33.2 | 15, 26, 17, 14 |
| 17 | 5.40 | t | 9.4 | 16, 18 | 17 | 138.7 | 16, 19, 26 |
| 18 | 5.89 | t | 10.8 | 19, 17 | 18 | 126.2 | 16, 20 |
| 19 | 6.34 | t | 13.3 | 18, 20 | 19 | 123.6 | 17, 21 |
| 20 | 5.55-5.58 | m | | 21, 19 | 20 | 131.8 | 22, 21, 18 |
| 21 | 5.45-5.50 | m | | 22, 20 | 21 | 70.7 | 22, 19, 20, 1 |
| 22 | 1.35 | d | 6.6 | 21 | 22 | 20.9 | 20, 21 |
| 23 | 1.44 | d | 6.9 | 2 | 23 | 12.3 | 3, 1, 2 |
| 24 | 1.06 | d | 7.7 | 8 | 24 | 12.7 | 9, 8, 7 |
| 25 | 1.32 | s | | | 25 | 28.8 | 9, 10, 11 |
| 26 | 0.97 | d | 6.6 | 16 | 26 | 16.9 | 16, 15, 17 |

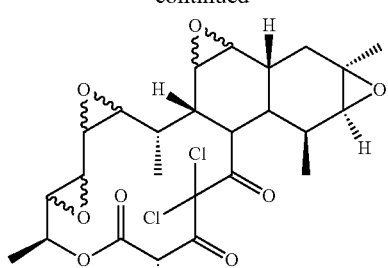

ChA-tetraEpo-B

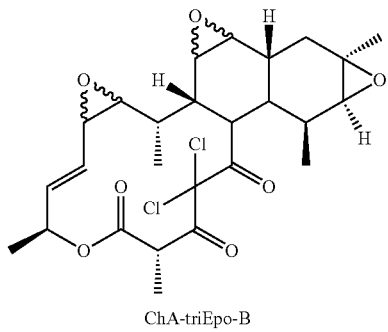

ChA-triEpo-B

Ch-A-Epo2 (0.02 mmol, 10 mg) was dissolved in chloroform (2 ml) and meta-Chloroperoxybenzoic acid (m-CPBA) (0.08 mmol, 14 mg) in chloroform (5 ml) was added to the solution dropwise over 30 min. The mixture was left stirring at room temperature for 16 hours. However, an aliquot of 0.5 ml was taken every 3 h, concentrated to dryness.

When no trace of starting material was observed (TLC: silica, $CHCl_3$: DCM, 1:1, UV, $R_f$), the remaining aliquot was joined with the latter ones and was concentrated under reduced pressure and the mixture was purified using flash chromatography (silica, $CHCl_3$:DCM, 1:1, UV) to yield the following derivatives as white powder.

Ch-A-tetraEpo-A HRMS (ESI, +ve) $C_{26}H_{32}Cl_2O_8$ $[M+H]^+$ calculated for 543.1547, found 543.1551;

Ch-A-tetraEpo-B HRMS (ESI, +ve) $C_{26}H_{32}Cl_2O_8$ $[M+H]^+$ calculated for 543.1547, found 543.1552;

Ch-A-triEpo-A HRMS (ESI, +ve) $C_{26}H_{32}Cl_2O_7$ $[M+H]^+$ calculated for 527.1598, found 527.1607;

Ch-A-triEpo-B HRMS (ESI, +ve) $C_{26}H_{32}Cl_2O_7$ $[M+H]^+$ calculated for 527.1598, found 527.1606

Results

TABLE 1

Water solubility of selected compounds

| Compound | Method 1 | Method 2 |
|---|---|---|
| Chlorotonil A (ChA) | 3 µg/mL ± 0.4 | 1.8 µg/mL |
| ChA-Epo2 | 14 µg/mL ± 0.3 | 10.3 µg/mL |
| ChA-Epo2-Cl | 280 µg/mL ± 0.4 | 320 µg/mL |
| ChA-Epo2-$ONO_2$ | 310 µg/mL ± 0.5 | 380 µg/mL |

TABLE 2

MIC values in µg/mL of various chlorotonil derivatives against Gram-positive bacteria and a sensitive *E. coli* strain (nd: not determined).

| | MIC [µg/ml] | | | |
|---|---|---|---|---|
| Compound | *B. subtilis* DSM-10 | *C. glutamicum* DSM-20300 | *S. aureus* Newman | *E. coli* TolC (+PMBN) |
| Chlorotonil A (ChA) | 0.0125 | 0.0125 | 0.0125 | 0.4 |
| ChA-Epo2 | 0.025 | 0.05 | 0.025 | 0.1 |
| ChA-Epo1 | 3.2 | >3.2 | 3.2 | >3.2 |
| ChA-Epo2-OBuOH | >3.2 | 3.2 | >3.2 | 1.6 |
| ChA-Epo2-OMe | >3.2 | >3.2 | 8-4 | 3.2 |
| ChA-Epo2-OBu | 0.8 | >3.2 | 1.6 | >3.2 |
| ChA-Epo2-Oisoamyl | 0.8 | 3.2 | 1.6 | 0.8 |
| ChA-Epo2-Br | 0.05 | 0.1 | 0.05 | 0.2 |
| ChA-Epo2-Cl | 0.1 | 0.4 | 0.05 | 0.8 |
| ChA-Epo2-OEt | >3.2 | >3.2 | 4-2 | >3.2 |
| ChA-Epo2-OH | >6.4 | >6.4 | 8-4 | >6.4 |
| ChA-Epo2-$ONO_2$ | 0.025 | 0.1 | 0.025 | 0.1 |
| ChA-Epo2-OBn | 0.4 | 3.2 | 0.4 | >3.2 |
| ChA-Epo2-glycerol | >3.2 | >3.2 | 4 | >3.2 |
| ChA-Epo2-F | 0.2 | 0.4-0.8 | 0.2 | 0.8 |
| ChA-Epo1-Cl | 3.2 | >3.2 | 3.2 | 3.2 |
| ChA-Epo1-OMe | 6.4 | >6.4 | 1.6 | 0.8-1.6 |
| ChA-Epo1-OEt | >6.4 | >6.4 | >1.6 | 1.6 |
| Chlorotonil B (ChB) | 0.2 | 0.1 | 0.2 | >3.2 |
| ChB-Epo | nd | nd | 0.05 | nd |
| ChB-Epo-Cl | nd | nd | 0.2 | nd |

TABLE 3

$IC_{50}$ values in nM of various chlorotonil derivatives against *P. falciparum* 3D7 (sensitive strain) and *P. falciparum* Dd2 (resistant strain).

| Compound | *P. falciparum* 3D7 | *P. falciparum* Dd2 |
|---|---|---|
| Chloroquine (reference) | 7.4 | 291.5 |
| Chlorotonil A (ChA) | 18.7 | 20.7 |
| ChA-Epo1 | 96.5 | 229.4 |
| ChA-Epo2 | 51.3 | 87.1 |
| ChA-Epo2-OMe | >11 µM | >11 µM |
| ChA-Epo2-OEt | >11 µM | >11 µM |
| ChA-Epo2-OBu | >11 µM | >11 µM |
| ChA-Epo2-Oisoamyl | >11 µM | >11 µM |
| ChA-Epo2-Cl | 38.7 | 45.9 |
| ChA-Epo2-Br | 25.1 | 64.4 |
| ChA-Epo1-Cl | >2095 | >2095 |
| ChA-Epo2-OH | >2168 | >2168 |
| ChA-Epo2-glycerol | >1895 | >1895 |
| ChA-Epo2-F | 135.6 | 328.8 |
| ChA-Epo2-$ONO_2$ | 0.92 | 2.2 |
| Chlorotonil B (ChB) | 96.6 | 63.6 |
| ChB-Epo | 158.1 | 182.0 |

TABLE 4

$IC_{50}$ values in nM of various chlorotonil derivatives against the L-929 cell line.

| Compound | L-929 (murine fibroblasts) |
|---|---|
| Chlorotonil A (ChA) | 1100 |
| ChA-Epo1 | 10300 |
| ChA-Epo2 | 2100 |
| ChA-Epo2-OMe | >100,000 |
| ChA-Epo2-OEt | >100,000 |
| ChA-Epo2-OBu | 49400 |
| ChA-Epo2-Oisoamyl | 44700 |
| ChA-Epo2-Cl | 4200 |
| ChA-Epo2-Br | 1100 |

TABLE 5

MIC values in µg/mL of various chlorotonil derivatives against a range of Gram-positive bacteria

| bacterial strain | ChA | ChA-Epo2 | ChB | ChB-Epo | ChB1-Epo |
|---|---|---|---|---|---|
| S. epidermidis 28765 | 0.1 | 0.2 | >3.2 | 0.8 | 0.05 |
| E. faecalis 20478 | 0.05 | 0.8 | >3.2 | 3.2 | 0.8 |
| E. faecalis 29212 | 0.05 | 1.6 | >3.2 | >3.2 | 0.8 |
| E. faecium 17050 (VRE) | 0.025 | 0.4 | >3.2 | 3.2 | 32 |
| E. faecium 20477 | 0.1 | 3.2 | >3.2 | >3.2 | 0.2 |
| M. luteus | 0.0125 | 0.025 | 0.4 | 0.1 | 0.0125 |
| M. smegmatis | 0.8 | 0.003 | 0.0125 | >3.2 | 16 |
| B. megaterium | 0.003 | 0.00125 | 0.1 | 0.05 | 0.0125 |
| S. pneumoniae 20566 | 0.006 | 0.2 | 1.6 | 0.8 | 0.4 |
| S. pneumoniae 11865 (PRSP) | 0.2 | 8 | >16 | >32 | — |

TABLE 6

Observations noted on fish larvae of AB line at five dpf (incubation started at two dpf)

| | ChA-Epo2 | ChB-Epo |
|---|---|---|
| 100 µM | died | died |
| 50 µM | died | died |
| 25 µM | died | OK |
| 10 µM | died | OK |
| 1 µM | OK | OK |
| MTC | 1 µM | 25 µM |

TABLE 7

Observations noted on fish larvae of TLF line at five dpf (incubation started at one dpf)

| | ChA-Epo2 | ChB-Epo |
|---|---|---|
| 100 µM | — | tail malformation |
| 50 µM | — | slight tail malformation |
| 25 µM | 1 died, 4 delayed in development | OK |
| 10 µM | 4 delayed in development | — |
| 1 µM | OK | — |
| MTC | 1 µM | 25 µM |

The chlorotonil derivatives of the present invention are superior in their pharmaceutical properties and structurally different to the known naturally produced chlorotonils. The invention demonstrates a very efficient chemistry. The two-step transformations applied are scalable to multi-gram scale and easily handled. The setup does not require any anhydrous systems or any complicated setups. All reactions are done at room temperature and the purification on both steps is done using normal phase chromatography, which facilitates the efficient upscaling of such systems. None of the used reagents is highly priced. All these facts display a system that can be applied in any lab set up and can be utilized for large-scale process development.

Due to the introduction of an epoxide on one of the double bonds and subsequent addition of a number of different substituents, the aqueous solubility could be increased when compared to the parent compound. A significant improvement in water solubility of chlorotonil from less than 2 µg/mL to over 300 µg/mL for some of the derivatives was observed (Table 1). This has helped in determining the maximum tolerated concentration (MTC) of the epoxide derivatives on two zebrafish lines (Tables 6 and 7), whereas this was not possible on the natural derivatives because of their low solubility. The derivatives were assessed in a number of biological assays and were shown to exhibit a broad antibiotic activity in the low nM range against a range of Gram-positive bacteria (Table 5), where additionally, some of the derivatives were intriguingly active on *Plasmodium falciparum* without displaying significant toxicity on a model cell line (Tables 2 to 4).

The invention claimed is:

1. A compound of general formula (I):

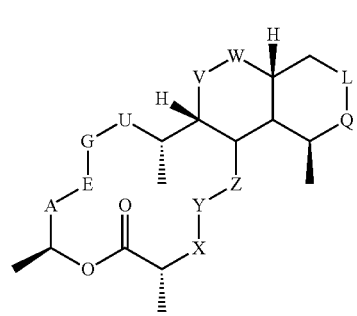

wherein
A-E together are a group of formula

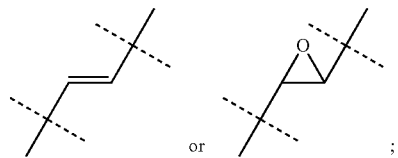

G-U together are a group of formula

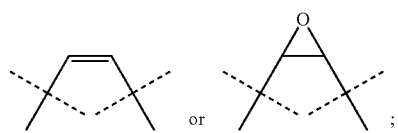

V-W together are a group of formula

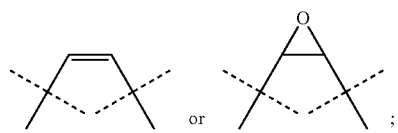

L-Q together are a group of formula

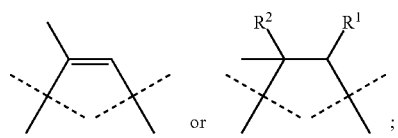

X-Y-Z together are a group of formula —C(=O)—C(Cl)$_2$—C(=O)—, —C(OH)=C(Cl)—C(=O)— or —C(=O)—C(Cl)=C(OH)—;

$R^1$ is a hydrogen atom, a halogen atom, NO$_2$, ONO$_2$, N$_3$, OH, NH$_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and $R^2$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or $R^1$ and $R^2$ together are a group of formula —O—;

with the proviso that all of A-E, G-U, V-W and L-Q do not at the same time possess a double bond;

or a pharmaceutically acceptable salt, solvate or hydrate or a pharmaceutically acceptable formulation thereof.

2. A compound according to claim 1 of general formula (II):

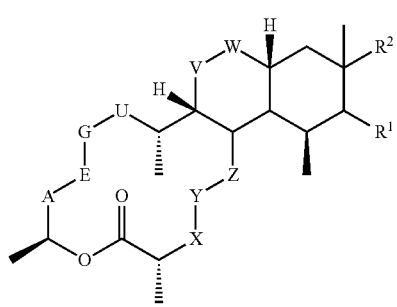

(II)

wherein
A-E together are a group of formula

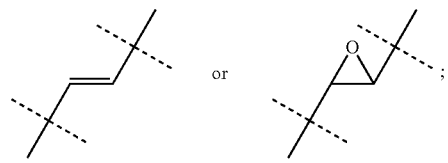

G-U together are a group of formula

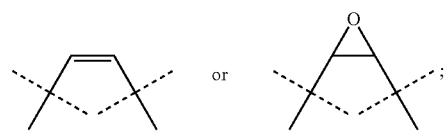

V-W together are a group of formula

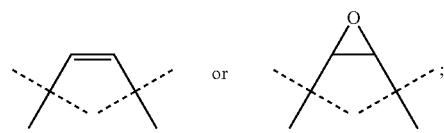

X-Y-Z together are a group of formula —C(=O)—C(Cl)$_2$—C(=O)—, —C(OH)=C(Cl)—C(=O)— or —C(=O)—C(Cl)=C(OH)—;

$R^1$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and $R^2$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or $R^1$ and $R^2$ together are a group of formula —O—;

or a pharmaceutically acceptable salt, solvate or hydrate or a pharmaceutically acceptable formulation thereof.

3. A compound according to claim 1 of general formula (III):

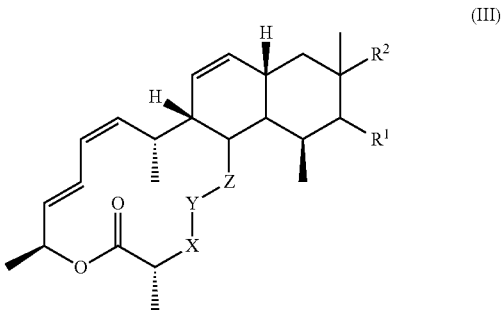

(III)

wherein
X-Y-Z together are a group of formula —C(=O)—C(Cl)$_2$—C(=O)—, —C(OH)=C(Cl)—C(=O)— or —C(=O)—C(Cl)=C(OH)—;

$R^1$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and $R^2$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or $R^1$ and $R^2$ together are a group of formula —O—;

or a pharmaceutically acceptable salt, solvate or hydrate or a pharmaceutically acceptable formulation thereof.

4. A compound according to claim 1 of general formula (IV):

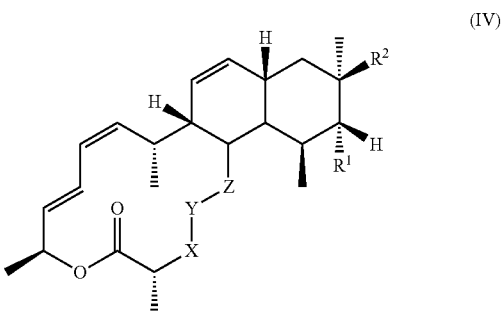

(IV)

wherein
X-Y-Z together are a group of formula —C(=O)—C(Cl)$_2$—C(=O)—, —C(OH)=C(Cl)—C(=O)— or —C(=O)—C(Cl)=C(OH)—;

$R^1$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; and $R^2$ is a hydrogen atom, a halogen atom, $NO_2$, $ONO_2$, $N_3$, OH, $NH_2$, SH, CN, or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

or a pharmaceutically acceptable salt, solvate or hydrate or a pharmaceutically acceptable formulation thereof.

5. A compound according to claim 1, wherein $R^1$ is a halogen atom, OH, $ONO_2$ or a group of formula —O—$C_{1-6}$ alkyl which group may be substituted by one or two hydroxy groups and/or by an optionally substituted phenyl group; and $R^2$ is OH.

6. A compound according to claim 1, wherein $R^1$ is OH; and $R^2$ is a halogen atom, OH, $ONO_2$ or a group of formula —O—$C_{1-6}$ alkyl which group may be substituted by one or two hydroxy groups and/or by an optionally substituted phenyl group.

7. A compound according to claim 1, wherein $R^1$ is F, Cl, Br, OH, $ONO_2$, OMe, OEt, OBu, OBuOH, Oisoamyl, OBn or glycerol; and $R^2$ is OH.

8. A compound according to claim 1, wherein $R^1$ is OH and $R^2$ is Cl, OMe or OEt.

9. A compound according to claim 1 having the following formula (V):

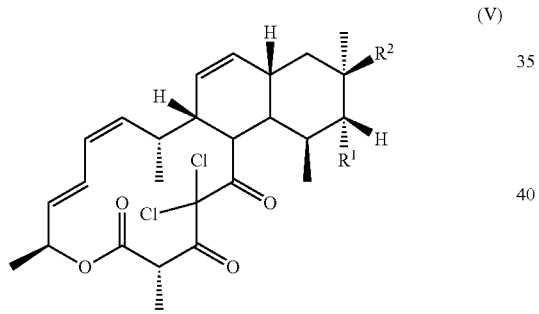

(V)

or a pharmaceutically acceptable salt, solvate or hydrate or a pharmaceutically acceptable formulation thereof.

10. A compound according to claim 1 having the following formula (VI):

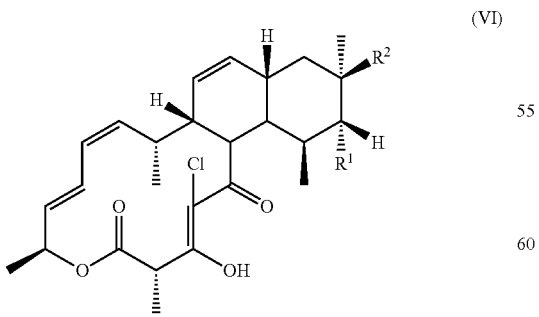

(VI)

or a pharmaceutically acceptable salt, solvate or hydrate or a pharmaceutically acceptable formulation thereof.

11. A compound according to claim 1 having the following formula (VII):

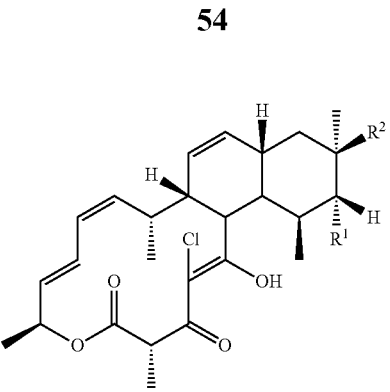

(VII)

or a pharmaceutically acceptable salt, solvate or hydrate or a pharmaceutically acceptable formulation thereof.

12. A compound according to claim 1 which is selected from the following compounds:

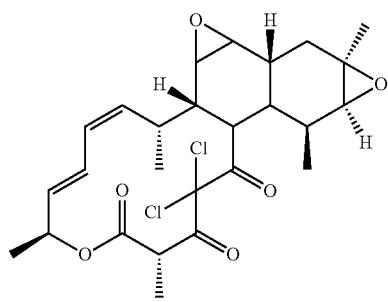

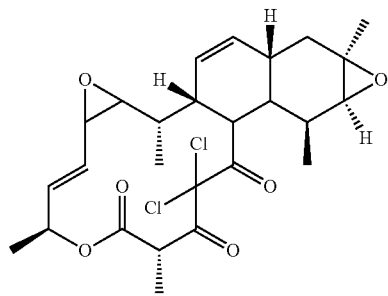

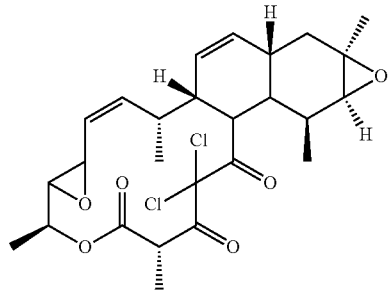

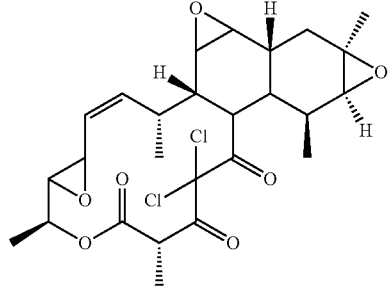

-continued

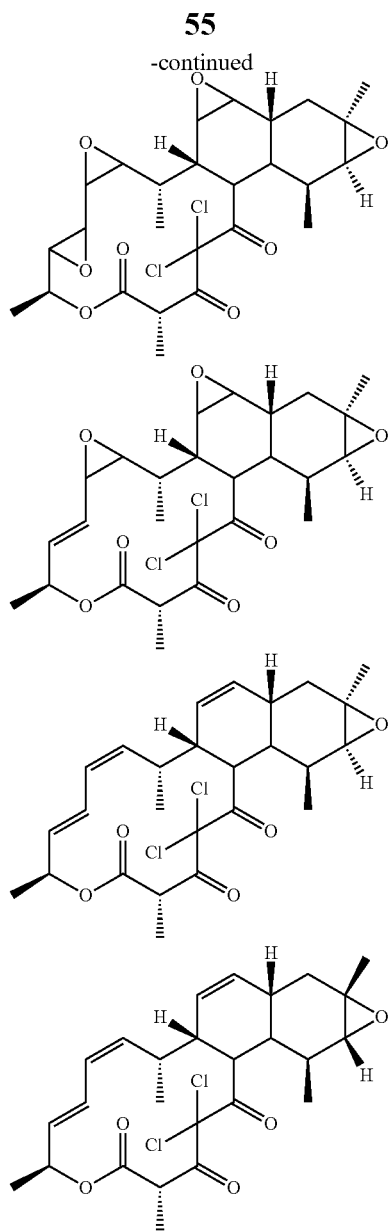

-continued

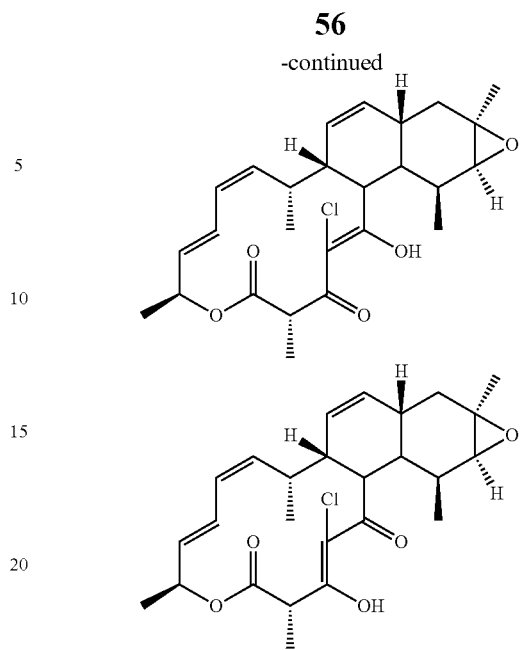

or a pharmaceutically acceptable salt, solvate or hydrate or a pharmaceutically acceptable formulation thereof.

13. Pharmaceutical composition comprising a compound according to claim 1 and optionally one or more carrier substances and/or one or more adjuvants.

14. A method for treating a subject suffering from or susceptible to a bacterial infection, comprising:
administering to the subject an effective amount of a compound of claim 1.

15. The method of claim 14, wherein the subject is identified as suffering from or susceptible to a bacterial infection and the compound is administered to the identified subject.

16. A method for treating a subject suffering from or susceptible to malaria, comprising:
administering to the subject an effective amount of a compound of claim 1.

17. The method of claim 16, wherein the subject is identified as suffering from or susceptible to malaria and the compound is administered to the identified subject.

* * * * *